US007976851B2

(12) United States Patent
Hodges et al.

(10) Patent No.: US 7,976,851 B2
(45) Date of Patent: Jul. 12, 2011

(54) NON-TOXIC BIOFILM INHIBITOR

(75) Inventors: Robert S. Hodges, Denver, CO (US);
Randall T. Irvin, Sherwood Park (CA);
Carmen Giltner, St. Albert (CA); Erin Van Schaik, Edmonton (CA)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 367 days.

(21) Appl. No.: 11/996,379

(22) PCT Filed: Jul. 21, 2006

(86) PCT No.: PCT/US2006/028353
§ 371 (c)(1),
(2), (4) Date: Jul. 1, 2008

(87) PCT Pub. No.: WO2007/089272
PCT Pub. Date: Aug. 9, 2007

(65) Prior Publication Data
US 2008/0287367 A1 Nov. 20, 2008

Related U.S. Application Data

(60) Provisional application No. 60/701,561, filed on Jul. 22, 2005.

(51) Int. Cl.
*A61K 39/108* (2006.01)
*A61K 39/00* (2006.01)
*A61K 39/02* (2006.01)

(52) U.S. Cl. ............... 424/260.1; 424/184.1; 424/185.1; 424/234.1; 530/300; 530/350

(58) Field of Classification Search ............... 424/184.1, 424/185.1, 234.1, 260.1; 530/300, 350
See application file for complete search history.

(56) References Cited

U.S. PATENT DOCUMENTS

| | | | |
|---|---|---|---|
| 5,223,604 A | 6/1993 | Hodges et al. | |
| 5,445,818 A | 8/1995 | Hodges et al. | |
| 5,468,484 A | 11/1995 | Hodges et al. | |
| 5,494,672 A * | 2/1996 | Hodges et al. | 424/260.1 |
| 5,612,036 A | 3/1997 | Hodges et al. | |
| 6,342,233 B1 | 1/2002 | Irvin et al. | |
| 6,475,434 B1 * | 11/2002 | Darouiche | 422/28 |
| 6,767,545 B2 | 7/2004 | Irvin et al. | |
| 2004/0071731 A1 | 4/2004 | Fitzgerald | |

FOREIGN PATENT DOCUMENTS

| | | |
|---|---|---|
| EP | 0 469 045 | 2/1992 |
| EP | 0 592 470 | 4/1994 |
| WO | WO 90/13563 | 11/1990 |
| WO | WO 92/12169 | 7/1992 |
| WO | WO 93/00358 | 1/1993 |
| WO | WO 01/10386 A2 | 2/2001 |
| WO | WO03/057900 * | 7/2003 |
| WO | WO 2007/089272 | 8/2007 |

OTHER PUBLICATIONS

Kus, J.V., et al. Microbiology, vol. 150, pp. 1315-1326, 2004.*
Cisar, J.O., et al. Advances in Dental Research, vol. 11, No. 1, pp. 168-175, 1997.*
Arnold et al. (Dec. 2004) "Multiple Imaging Techniques Demonstrate the Manipulation of Surfaces to Reduce Bacterial Contamination and Corrosion," *J. Microsc.* 216(3):215-221.
Audette et al. (2004) "Crystallographic Analysis of the *Pseudomonas aeruginosa* Strain K122-4 Monomeric Pilin reveals a Conserved Receptor-Binding Architecture," *Biochemistry* 43(36):11427-11435.
Bagge et al. (May 2001) "*Shewanella putrefaciens* Adhesion and Biofilm Formation on Food Processing Surfaces," *Appl. Environ. Microbiol.* 67(5):2319-2325.
Balazs et al. (2004) "Inhibition of Bacterial Adhesion on PVC Endotracheal Tubes by RF-Oxygen Glow Discharge, Sodium Hydroxide and Silver Nitrate Treatments," *Biomaterials* 25:2139-2151.
Beachy, E.H. (Mar. 1981) "Bacterial Adherence: Adhesion-Receptor Interactions Mediating the Attachment of Bacteria to Mucosal Surfaces," *J. Infect. Dis.* 143(3):325-345.
Blenkinsopp et al. (Nov. 1992) "Electrical Enhancement of Biocide Efficacy Against *Pseudomonas aeruginosa* Biofilms," *Appl. Environ. Microbiol.* 58(11):3770-3773.
Bodey et al. (Mar.-Apr. 1983) "Infections Caused by *Pseudomonas aeruginosa*," *Rev. Infect. Dis.* 5(2):279-313.
Bremer et al. (Jul. 1991) "Laboratory-Based Model of Microbiologically Induced Corrosion of Copper," *Appl. Environ. Microbiol.* 57(7):1656-1962.
Campbell et al. (1995) "Comparison of NMR Solutions Structures of the Receptor Binding Domains of *Pseudomonas aeruginosa* Pili Strains PAO, KB7, and PAK: Implications for Receptor Binding and Synthetic Vaccine Design," *Biochemistry* 34(50):16255-16268.
Characklis et al. (1990) "Physiological Ecology in Biofilm Systems," In; *Biofilms*, Characklis et al. eds., New York: John Wiley and Sons, pp. 341-394.
Costerton, J.W. (Feb. 2001) "Cystic Fibrosis Pathogenesis and the Role of Biofilms in Persistent Infection," *Trend Microbiol.* 9(2):50-52.
Craig et al. (May 2003) "Type IV Pilin Structure and Assembly: X-Ray and EM Analysis of Vibrio Cholerae Toxin-Coregulated Pilus and *Pseudomonas aeruginosa* PAK Pilin," *Mol. Cell.* 11:1139-1150.
Doig et al. (Jan. 1990) "Inhibition of Pilus-Mediated Adhesion of *Pseudomonas aeruginosa* to Human Buccal Epithelial Cells by Monoclonal Antibodies Directed Against Pili," *Infect. Immun.* 58(1):124-130.

(Continued)

*Primary Examiner* — Rodney P. Swartz
(74) *Attorney, Agent, or Firm* — King & Spalding LLP; Peter J. Dehlinger; Greenlee, Winner & Sullivan, P.C.

(57) ABSTRACT

The present invention relates to a composition and method for preventing or inhibiting biofilm formation on biotic or abiotic surfaces. The composition comprises a peptide based on the C-terminal receptor binding domain of *Pseudomonas aeruginosa* type IV pilin, which binds to an abiotic surface (e.g., steel, plastic) with high affinity and prevents binding of a variety of *P. aeruginosa* strains to the surface. The inventive composition represents a non-toxic inhibitor for biofilm formation, particularly on an abiotic surface, which is responsible for a large number of problematic diseases and massive economic losses. The inventive method is useful as a safe and environmentally friendly means of modifying a surface of a variety of biomedical, nanotechnological, and biotechnological devices or articles.

13 Claims, 8 Drawing Sheets

OTHER PUBLICATIONS

Folkhard et al. (1981) "Structure of Polar Pili from *Pseudomonas aeruginosa* Strains K and O," *J. Mol. Biol.* 149:79-93.

Giltner et al. (2006) "The *Pseudomonas aeruginosa* Type IV Pilin Receptor Binding Domain Functions as an Adhesion for Both Biotic and Abiotic Surfaces," *Mol. Microbiol.* 59(4):1083-1096.

Groessner-Schreiber et al. (2004) "Do Different Implant Surfaces Exposed in the Oral Cavity of Humans Show Different Biofilm Compositions and Activities," *Eur. J. Oral Sci.* 112:516-522.

Hazes et al. (2000) "Crystal Structure of *Pseudomonas aerginosa* PAK Pilin Suggests a Main-Chain-Dominated Mode of Receptor Binding," *J. Mol. Biol.* 299:1005-1017.

Hood et al. (1997) "Adherence to Stainless Steel by Foodborne Microorganisms During Growth in Model Food Systems," *Int. J. Food. Microbiol.* 37:145-153.

Irvin et al. (Dec. 1989) "Characterization of the *Pseudomonas aeruginosa* Pilus Adhesion: Conformation that the Pilin Structural Protein Subunit Contains a Human Epithelial Cell-Binding Domain," *Infect. Immun.* 57(12):3720-3726.

Irvin et al. (1990) "Usefulness of Equilibrium Parameters of Adhesion in Predicting the Outcome of Competition for Bacterial Receptor Sires on Respiratory Epithelial Cells by *Pseudomonas aeruginosa* Strains of Heterologous Pilus Type," *Microbial. Ecol. Health Dis.* 3:39-47.

Jonhansen et al. (Sep. 1997) "Enzymatic Removal and Disinfection of Bacterial Biofilms," *Appl. Environ. Microbiol.* 63(9):3724-728.

Khaled et al. (2001) "Method for Studying Development of Colonization and Infection of Dialysis Catheters," *Adv. Perit. Dial.* 17:163-171.

Klausen et al. (2003) "Involvement of Bacterial Migration in the Development of Complex Multicellular Structures in *Pseudomonas aeruginosa* Biofilms," *Mol. Microbiol.* 50(1):61-68.

Koga et al. (Apr.1993) "Genetic and Functional Characterization of the Gene Cluster Specifying Expression of *Pseudomonas aeruginosa* Pili," *Infect. Immun.* 61(4):1371-1377.

Kus et al. (2004) "Significant Differences in Type IV Pilin allele Distribution Among *Pseudomonas aeruginosa* Isolated from Cystic Fibrosis (CF) Versus non-CF Patients," *Microbiology* 150:1315-1326.

Leake et al. (Feb. 1982) "Use of Chemotaxis Chambers for Studying in Vitro Bacterial Colonization of Biomaterials," *J. Clin. Microbiol.* 15(2):320-323.

Lee et al. (1994) "The Binding of *Pseudomonas aeruginosa* Pili to Glycoshyingolipids is a Tip-Associated Event Involving the C-Terminal Region of the Structural Pilin Subunit," *Mol. Microbiol.* 11(4):705-713.

Lee et al. (Feb. 1989) "Immunological Studies of the Disulfide Bridge Region of *Pseudomonas aeruginosa* PAK and PAO Pilins, Using Anti-PAK Pilus and Antipeptide Antibodies," *Infect. Immun.* 57(2):520-526.

Lomander et al. (2004) "Evaluation of Chlorines' Impact on Biofilms on Scratched Stainless Steel Surfaces," *Bioresour. Technol.* 94:275-283.

Mattick, J.S. (2002) "Type IV Pili and Twitching Motility," *Ann. Rev. Microbiol.* 56:289-314.

McEachran et al. (1985) "A New Method for the Irreversible Attachment of Cells or Proteins to Polystyrene Tissue Culture Plates for Use in the Study of Bacterial Adhesion," *J. Microbiol. Methods* 5:99-111.

McNeil et al. (Aug. 1, 2001) "Outbreak of Sternal Surgical Site Infections Due to *Pseudomonas aeruginosa* Traced to a Scrub Nurse with Onychomycosis," *Clin. Infect. Dis.* 33:317-323.

O'Toole et al. (1998) "Flagellar and Twitching Motility are Necessary for *Pseudomonas aeruginosa* Biofilm Development," *Mol. Microbiol.* 30(2):295-304.

O'Toole et al. (2000) "Biofilm Formation as Microbial Development," *Ann. Rev. Microbiol.* 54:49-79.

Paranchych et al. (1979) "Biochemical Studies on Pili Isolated from *Pseudomonas aeruginosa* Strain PAO," *Can. J. Microbiol.* 25:1175-1181.

Pasloske et al. (Aug. 8, 1988) "Two Unusual Pilin Sequences from Different Isolated of *Pseudomonas aeruginosa*," *J. Bacteriol.* 170:3738-3741.

Pier, G.B. (Apr. 1985) "Pulmonary Disease Associated with *Pseudomonas aeruginosa* in Cystic Fibrosis: Current Status of the Host-Bacterium Interaction," *J. Infect. Dis.* 151(4):575-580.

Saiman et al. (Mar. 1990) "The Effect of Piliation and Exoproduct Expression on the Adherence of *Pseudomonas aeruginosa* to Respiratory Epithelial Monolayers," *J. Infect. Dis.* 161:541-548.

Schweizer et al. (1998) "Interaction Between the Pili of *Pseudomonas aerginosa* PAK and its Carbohydrate Receptor β-D-GaINAc (1-4) β-D-Gal Analogs," *Can. J. Microbiol.* 44:307-311.

Sheth et al. (1994) "The Pili of *Pseudomonas aeruginosa* Strains PAK and PAO Bind Specifically to the Carbohydrate Sequence βGaINAc (1,4) βGal Found in Glycoshingolipids asialo-$GM_1$ and asialo-$GM_2$," *Mol. Microbiol.* 11(4):715-723.

Sheth et al. (1995) "Development of an Anti-Adhesive Vaccine for *Pseudomonas aeruginosa* Targeting the C-Terminal Region of the Pilin Structural Protein," *Biomed. Pept. Protein Nuc. Acid* 1:141-148.

Singh et al. (Oct. 12, 2000) "Quorum-Sensing Signals Indicate that Cystic Fibrosis Lungs are Infected with Bacterial Biofilms," *Nature* 407:762-764.

Sreekumari et al. (2001) "Bacterial Attachment to Stainless Steel Welds: Significance of Substratum Microstructure," *Biofouling* 17:303-316.

Stanley, P.M. (1983) "Factors Affecting the Irreversible Attachment of *Pseudomonas aeruginosa* to Stainless Steel," *Can. J. Microbiol.* 29:1493-1499.

Starnbach et al. (1992) "The FliA (rpoF) Gene of *Pseudomonas aeruginosa* Encodes as Alternative Sigma Factor Required for Flagellin Synthesis," *Mol. Microbiol.* 6:459-469.

Stoodley et al. (2002) "Biofilms as Complex Differentiated Communities," *Ann. Rev. Microbiol.* 56:187-209.

Suci et al. (2001) "Comparison of Adsorptive Behavior of Two *Mytilus edulis* Foot Proteins on Three Surfaces," *Colloid Surface Biointerface* 22:159-168.

Traverso et al. (2005) "Long Term Effect on IOP of a Stainless Steel Glaucoma Drainage Implant (Ex-PRESS) in Combined Surgery with Phacoemulsification," *Br. J. Opthalmol.* 89:425-429.

Tredget et al. (1992) "Epidemiology of Infections with *Pseudomonas aeruginosa* in Burn Patients: The Role of Hydrotherapy," *Clin. Infect. Dis.* 15:941-949.

VanHaecke et al. (Mar. 1990) "Kinetics of *Pseudomonas aeruginosa* Adhesion to 304 and 316-L Stainless Steel: Role of Cell Surface Hydrophobicity," *Appl. Environ. Microb.* 56(3):788-795.

Van Schaik et al. (Feb. 2005) "DNA Binding: A Novel Function of *Pseudomonas aeruginosa* Type IV Pili," *J. Bacteriol.* 187(4):1455-1494.

Watnick et al. (May 2000) "Biofilm, City of Microbes," *J. Bacteriol.* 182(10):2675-2679.

Wong et al. (1995) "Structure-Function Analysis of the Adherence-Binding Domain on the Pilin of *Pseudomonas aeruginosa* Strains PAK and KB7," *Biochemistry* 34(40):12963-12972.

Wong et al. (1992) "Antigen-Antibody Interaction: Elucidation of the Epitope and Strain-Specificity of a Monoclonal Antibody Directed Against the Pilin Protein Adherence Binding Domain of *Pseudomonas aeruginosa* Strain K," *Protein Sci.* 1:1308-1318.

Wozniak et al. (Jun. 24, 2003) "Alginate is not a Significant Component of the Extracellular Polysaccharide Matrix of PA14 and PAO1 *Pseudomonas aeruginosa* Biofilms," *Proc. Nat. Acad. Sci. USA* 100(13):7907-7912.

Yu et al. (1996) "Use of Synthetic Peptides to Confirm that the *Pseudomonas aeruginosa* PAK Pilus Adhesion and the *Candida albicans* Fimbrial Adhesion Possess a Homologous Receptor-Binding Domain," *Mol. Microbiol.* 19(5):1107-1116.

Zuo et al. (2005) "Aluminum- and Mild Steel-Binding Peptides from Phage Display," *Appl. Microbiol. Biotechnol.* 68:505-509.

Kumon et al., 1997. Can J Urol. Sep;4(3):416-421. Fully hydrated images of *Pseudomonas aeruginosa* biofilm on the surface of catheter material. Kumon H, Watanabe T, Vincent P, Nickel JC. Abstract.

International Application No. PCT/US2006/028353, International Search Report, 4 pages, May 20, 2010.

Publication of International Search Report, WO 2007/089272 A3, Jul. 29, 2010, 4 pages.

\* cited by examiner

NON-TOXIC BIOFILM INHIBITOR

CROSS-REFERENCE TO RELATED APPLICATIONS

This application is the U.S. National Stage of International Application No. PCT/US2006/028353, filed Jul. 21, 2006, which claims the benefit of U.S. Provisional Application No. 60/701,561, filed Jul. 22, 2005, both of which are incorporated herein by reference in entirety.

STATEMENT ON U.S. FEDERALLY SPONSORED RESEARCH OR DEVELOPMENT

This invention was made with government support under NIH Grant No. R01 A148717 awarded by the National Institutes of Health. The government has certain rights in the invention.

BACKGROUND OF THE INVENTION

The present invention relates to a composition and method for preventing or inhibiting biofilm formation on a surface, particularly an abiotic surface, using the composition.

*Pseudomonas* is a gram negative bacteria which is a notorious cause of nosocomial or hospital acquired infections. It is a significant pathogen in several clinical settings, especially in immunocompromised patients. *Psuedomonas aeruginosa* is the most common disease causing *Pseudomonas* species.

*Pseudomonas aeruginosa* is an effective and common opportunistic pathogen of humans, causing serious infections in cystic fibrosis, intensive care, burn, and immuno-compromised patients (Bodey et al., 1983; Pier, 1985; Costerton, 2001). Initial binding of the bacterium to an abiotic or a cellular substratum is considered by many to be the initial stage of colonization for both biofilm formation (Watnick and Kolter, 2000) and initiation of an infection (Beachey, 1981). Recently, *P. aeruginosa* biofilms have been implicated during chronic infection of cystic fibrosis patients (O'Toole et al., 2000; Singh et al., 2000). In addition to chronic infection, *P. aeruginosa* biofilms contribute to morbidity of patients with medical implants including catheters (Kumon et al., 1997; Khaled et al., 2001), prosthetics (McNeil et al., 2001) and stainless steel implants (Traverso et al., 2005).

Stainless steel is widely used, particularly in the food sector, and commonly used in the hospital environment and in medical devices (Hood et al., 1997). *P. aeruginosa* readily binds to stainless steel (Stanley, 1983; VanHaecke et al., 1990) to form biofilms (Leake et al., 1982; Blenkinsopp et al., 1992; Johansen et al., 1997). *P. aeruginosa* biofilms on stainless steel surfaces can serve as a significant hospital reservoir for the infection of susceptible patients (Tredget et al., 1992). Type IV pili are essential for the normal development of *P. aeruginosa* biofilms as mutants lacking the ability to form pili are unable to develop past the microcolony stage in static or flow biofilm systems (O'Toole and Kolter, 1998; Klausen et al., 2003).

Type IV pili are composed of a single pilin subunit, PilA, and are assembled into long polar surface appendages (Folkhard et al., 1981). This assembly process ensures that the receptor binding domain is only located at the tip of the pilus (Lee et al., 1994). The pilus-associated epithelial cell receptor binding domain is encoded in residues 128-144 of the C-terminal region of PilA, the pilin structural protein (Irvin et al., 1989a). This terminal binding domain specifically recognizes GalNAc-β-D-(1,4)-Gal moieties of asialo-GM$_1$ as a minimal receptor (Sheth et al., 1994). Adherence to this receptor is specific and can be inhibited by a synthetic receptor binding domain, PAK(128-144)ox, or by synthetic GalNAc-β-D-(1,4)-Gal (Sheth et al., 1994; Wong et al., 1995; Schweizer et al, 1998).

Although it has been recognized that biofilms are directly responsible for a large number of problematic diseases resulting in high mortality and morbidity and for massive losses in the economy by causing fouling of pipes, ships, and heat treatment equipment, prevention or modulation of biofilm formation has been extremely challenging. The currently available methods rely on extreme measures such as releasable antibiotics, colloidal silver deposition, laser ablation, and electric field pulses.

Accordingly, there is a need for a new composition and method for preventing or inhibiting biofilm formation on both biotic and abiotic surfaces. Towards this end, the present inventors discovered a composition which binds to an abiotic surface (e.g. steel) with high affinity and prevents binding of a variety of *P. aeruginosa* strains to the surface. Thus, the invention provides a new means of preventing or inhibiting biofilm formation. The advantage of the invention will become apparent by the following description.

SUMMARY OF THE INVENTION

Biofilm is a surface attached form of bacterial growth that is responsible for a large number of life-threatening diseases. The present invention provides a composition and method for preventing or inhibiting biofilm formation on a biotic or an abiotic surface. The composition comprises a peptide derived from the C-terminal portion of *Pseudomonas* type IV pilin, formerly identified as the receptor binding domain, and optionally a carrier agent.

This invention is based on the inventors' findings that 1) *Pseudomonas aeruginosa* binds to abiotic surfaces in a concentration-dependent, saturable manner during the initial stages of biofilm formation and that this binding is mediated by type IV pili, 2) a synthetic peptide, referred herein as PAK(128-144)ox, derived from the receptor binding domain of *P. aeruginosa* type IV pilin binds directly to steel with high affinity and inhibits the binding of a variety of homologous and heterologous *P. aeruginosa* strains to steel with an apparent Ki of approximately 4 nM, and 3) PAK type IV pili can also bind polystyrene and polyvinylchloride in a concentration-dependent and saturable manner. These findings are the first demonstration that such a peptide can bind to an abiotic surface with high affinity and prevent binding of other *Pseudomonas* strains to the same surface. Therefore, the invention provides a new method of preventing or inhibiting biofilm formation on a surface, particularly an abiotic surface, using the peptide. It is expected that the inventive composition and method would be applicable to prevent or inhibit biofilm formation caused by any bacteria, particularly any gram negative bacteria.

Given that certain amino acid residues in the receptor binding domain of the pilin peptide of a large number of *Pseudomonas* isolates are highly conserved, it is predicted that a peptide derived from the corresponding region (PAK128-144) of any *Pseudomonas*, particularly of any *P. aeruginosa* strain, would bind to steel with high affinity and inhibit biofilm formation. Tables 3 and 4 show the amino acid sequences of the C-terminal receptor binding domain of various *Pseudomonas aeruginosa* strains. Based on the sequence conservation and high prevalence of certain amino acid residues in a large number of *Pseudomonas* isolates, it is expected that a synthetic peptide of at least 10 amino acids in length (referred herein as the "core sequence"), preferably about 14 to 17 amino acids in length, having certain representative conserved amino acids as shown in Tables 3 and 4, or a longer peptide containing the core sequence would be useful to prevent or inhibit biofilm formation. The inventive peptide also includes those having mixed or hybrid amino acid sequences, i.e., portion of the amino acid residues from one strain (e.g. PAK) of *Pseudomonas* combined with those from another strain (e.g. PAO) (e.g. K-C-T-S-T-Q-D-E-Q-F-I-P-K-G-C-S-K; SEQ ID NO:1). Based on the amino acid sequence information shown in Tables 3 and 4, the inventive peptide can have a general core sequence, K/A/S/T-C-T/K/A-S/T-D/T/N-Q/V/A-D/E-E/IP/A/N-Q/M/K-F/Y-I/T/R/L-P-K/N-G/T-C-S/D/T/Q/N-K/N/D/T (SEQ ID NO:2). Also included in the present invention are those peptides having modifications (e.g. acetylation, amidation, methylation, carboxymethylation etc.) of one or more amino acid residues in the peptide.

Table 2 provides examples of the inventive peptide. Preferred peptides are those having one of the core sequences or a longer peptide containing one of the core sequences as given below:

```
                                              (SEQ ID NO: 3)
K-C-T-S-D-Q-D-E-Q-F-I-P-K-G-C-S-K (PAK 128-144)

(SEQ ID NO: 4)
A-C-K-S-T-Q-D-P-M-F-T-P-K-G-C-D-N (PAO 128-144)

(SEQ ID NO: 5)
S-C-A-T-T-V-D-A-K-F-R-P-N-G-C-T-D (KB7 128-144)

(SEQ ID NO: 6)
A-C-T-S-N-A-D-N-K-Y-L-P-K-T-C-Q-T (K122-4 128-144)

(SEQ ID NO: 7)
T-C-T-S-T-Q-E-E-M-F-I-P-K-G-C-N-K (CD4 128-144)
```

Most preferred peptide has a sequence K-C-T-S-D-Q-D-E-Q-F-I-P-K-G-C-S-K (PAK128-144; SEQ ID NO:3), which is characterized by two cysteine residues flanking 12 amino acids. A "carrier agent" as used herein is an agent (e.g., water, buffer, salt, solvent, etc.) that can stabilize the peptide (i.e. preserve functionality) and/or facilitate coating or delivery of the peptide to a given surface, biotic or abiotic. In this sense, the carrier agents of the present invention include pharmaceutically and physiologically acceptable carriers which are well known in the art.

The inventive composition is particularly useful in preventing or inhibiting biofilm formation on an abiotic surface of a device or an article. Examples of the devices and articles that can be treated with the inventive composition include, without limitation, medical implants including catheters, prosthetic devises, contact lens, hydrotherapy pools, ships, pipes, and the like. Examples of the type of the surface of a devise or an article that can be treated with the inventive composition include, but are not limited to, metal surfaces (e.g., steel, tin, aluminum, titanium, chromium or any metal that displays an oxide crystalline surface), plastic surfaces (e.g. contact lens, polyvinylchloride, polystyrene, and other plastic surfaces made of a range of synthetic and semisynthetic polymerization products, which are known in the art), glass, silicate, ceramics and the like.

DETAILED DESCRIPTION OF THE INVENTION

Figure 1:
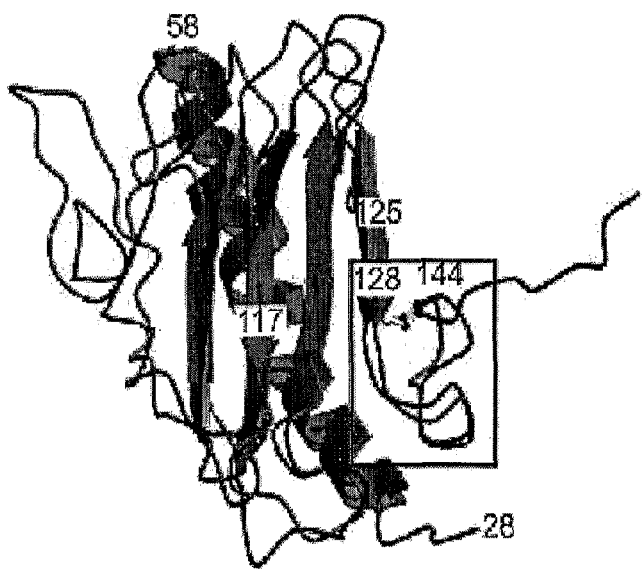
FIG. 1. (a) Full length pilin sequences of *Pseudomonas aeruginosa* strains PAK (SEQ ID NO:20), PAO SEQ ID NO: 21), KB7 (SEQ ID NO:22), and K122-4 (SEQ ID NO: 23). Boxed area represents di-sulfide loop region of residues 128-144 of the PAK sequence. The di-sulfide loop region contains an epithelial cell binding domain and displays a conserved antigenic epitope despite extensive sequence variation. (b) Structural overlay of *Pseudomonas aeruginosa* strains PAK and K122-4 truncated monomeric pilins. Di-sulfide loop region is highlighted by boxed area, cysteine residues are shown in black and the di-sulfide bonds are shown for PAK and K122-4 strains. (c) 15% SDS-PAGE gel (Sambrook et al., 1989), lane 2 shows pili preparation before final cesium chloride gradient and lane 3 shows a single non-contaminated band of pili after density ultacentrifugation. Lane 1 represents a pre-stained protein ladder (Fermentas Inc., Hanover, Md.). Epifluorescence micrograph of acridine orange stained PAK wild-type cells (d), and PAKNP (PilA.sup.-strain) (e) bound to stainless steel. Bacterial cells fluoresce orange, while grain boundaries fluoresce green due to non-specific staining. The bar represents 5 .mu.M. (f) Electron micrograph picture of PAK pili. The bar represents 100 nM.
Figure 1:
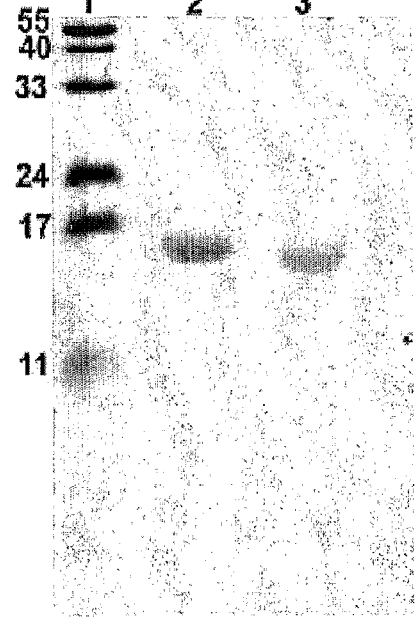
Figure 1:
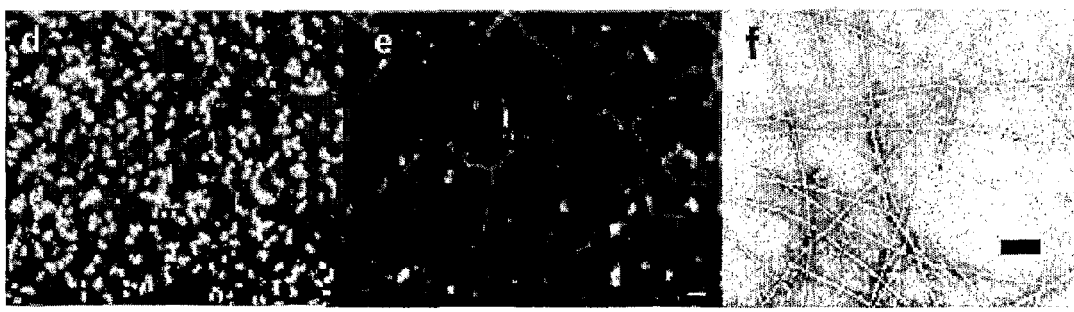

In general the terms and phrases used herein have their art-recognized meaning, which can be found by reference to standard texts, journal references and contexts known to those skilled in the art. The following definitions are provided to clarify their specific use in the context of the invention.

The term, "biofilm", as used herein, is a surface attached form of bacterial growth. The surface is either a biotic (e.g. cell surface) or abiotic surface (e.g. metal such as stainless steel). In the context of the present invention, it is expected that the inventive composition would prevent or inhibit biofilm formation caused by any bacteria, gram positive or gram negative. Since pili are present on the surface of most gram negative bacteria, it is predicted that the inventive peptide would be particularly useful for preventing or inhibiting biofilm formation caused by any gram negative bacteria, particularly those of *Pseudomonas* genus. The genus *Pseudomonas* contains more than 140 species, more than 25 of which are associated with humans. *Pseudomonads* known to cause disease in humans include *P aeruginosa, P fluorescens, P putida, P cepacia, P stutzeri, P maltophilia, P putrefaciens, P mallei* and *P pseudomallei*, all of which express type IV pili. For detailed description of gram positive and negative bacteria, and *Pseudomonas*, see "Medical Microbiology", 3$^{rd}$ Edition edited by Samuel Baron, 1991, Churchill Livingstone Inc. New York, USA.

The inventive peptides disclosed herein are derived from the receptor binding domain of the C-terminal region of the type IV pilin protein of *Pseudomonas*. Accordingly, a peptide of at least 10 amino acids or longer derived from the corresponding region of PAK128-144 from any *Pseudomonas* pilin protein is expected to have similar activities as shown herein with PAK128-144 peptide. The inventive peptides include those with certain modifications (e.g. acetylation and/or amidation) which do not affect the binding activity to abiotic surfaces. Types and methods of peptide modifications are well known in the art ("Fmoc Solid-Phase Peptide Synthesis: A Practical Approach". 2000 W. C. Chan and P. D. White (Eds.) Oxford University Press, England.

The amount of the inventive composition sufficient to prevent or inhibit biofilm formation on a given surface will vary depending on a variety of factors, for example, the type of the surface or type of the bacteria causing the biofilm formation, mode of application, and the carrier agent with which the composition is applied to the surface. However, a skilled artisan would understand how to determine the "optimal concentration" of the inventive composition necessary to prevent or inhibit biofilm formation on an abiotic surface by carrying out routine experimentations (e.g. dose-response curve, inhibition kinetics), as disclosed in the Examples sections and the information readily available in the art.

The term, "carrier agent", is used herein to indicate a component of the inventive composition, which is used, for example, to stabilize the inventive peptide and/or to facilitate application of the peptide to a surface without affecting the functionality of the peptide. Examples include, but are not limited to, water, buffer (pH about 5-8, e.g. phosphate, tris etc), salt (e.g. sodium chloride about 5-10 mM), and solvent (e.g. methanol about 1-20%). Preferred carrier agent is phosphate buffer (pH 7.2) containing 0-10% methanol and 10 mM sodium chloride. The term "carrier agent", as used herein, is also intended to include what is commonly referred to as the "pharmaceutically or physiologically acceptable carrier or salt" since the inventive composition is also useful for preventing or inhibiting biofilm formation on a biotic surface (e.g. cell surface). Accordingly, the carrier agents include those carboxylate salts or acid addition salts of the peptide of the present invention which are suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "pharmaceutically acceptable salt" in general refers to the relatively nontoxic, inorganic and organic acid addition salts of the compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. See, for example, Berge S. M, et al., Pharmaceutical Salts, J. Pharm. Sci. 66:1-19 (1977) which is incorporated herein by reference. Similarly, when the term "carrier agent" is synonymously used as "pharmaceutically acceptable carrier," it is an organic or inorganic composition which serves as a carrier/stabilizer/diluent of the active ingredient (i.e., peptide) of the present invention in a pharmaceutical composition. In certain cases, the pharmaceutically acceptable carriers are salts. Further examples of pharmaceutically acceptable carriers include but are not limited to water, phosphate-buffered saline, saline, pH controlling agents (e.g. acids, bases, buffers), stabilizers such as ascorbic acid, isotonizing agents (e.g. sodium chloride), aqueous solvents, a detergent (ionic and non-ionic) such as polysorbate or TWEEN 80.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Trp, Tryptophan; Y, Tyr, Tyrosine.

*Pseudomonas aeruginosa* readily binds to stainless steel or plastic (e.g. polyvinylchloride, polystyrene) surfaces causing major problems in both the medical and food industries. In the studies disclosed herein, we examined the initial event of *P. aeruginosa* biofilm formation on stainless steel and plastic, the binding of the organism to the surface. We found that *P. aeruginosa* binds in a concentration dependent, saturable manner during the initial stage of biofilm formation. *P. aeruginosa* type IV pili mediate binding to stainless steel as a PilA$^-$ strain does not bind to steel, purified type IV pili bound in a concentration-dependent, saturable manner, and pili competitively inhibited whole cell binding. Antibodies specific for the *P. aeruginosa* stain K (PAK) type IV pili (rabbit polyclonal antibody and monoclonal antibodies PK99H and PK3B) prevented adherence of both viable cells and purified pili to steel. As antibodies specific for the C-terminal PilA receptor binding domain inhibited adherence, the role of the PilA receptor binding domain in mediating binding to steel surfaces was examined. A synthetic peptide of the PAK PilA epithelial cell receptor binding domain (PAK(128-144)ox) bound directly to steel with a very high affinity. The interaction of pili with steel was specifically inhibited by this peptide with an apparent Ki of ~0.2 nM and specifically inhibited the binding of viable homologous and heterologous *P. aeruginosa* strains to steel with an apparent Ki of ~4 nM. Therefore, the C-terminal PilA receptor binding domain mediates binding to both biotic and abiotic surfaces, although this binding function appears to be optimized for binding to abiotic surfaces rather than for adherence during the infectious process.

Initial Colonization of Stainless Steel is Dependent upon Type IV Pili in *P. aeruginosa*

Figure 2:
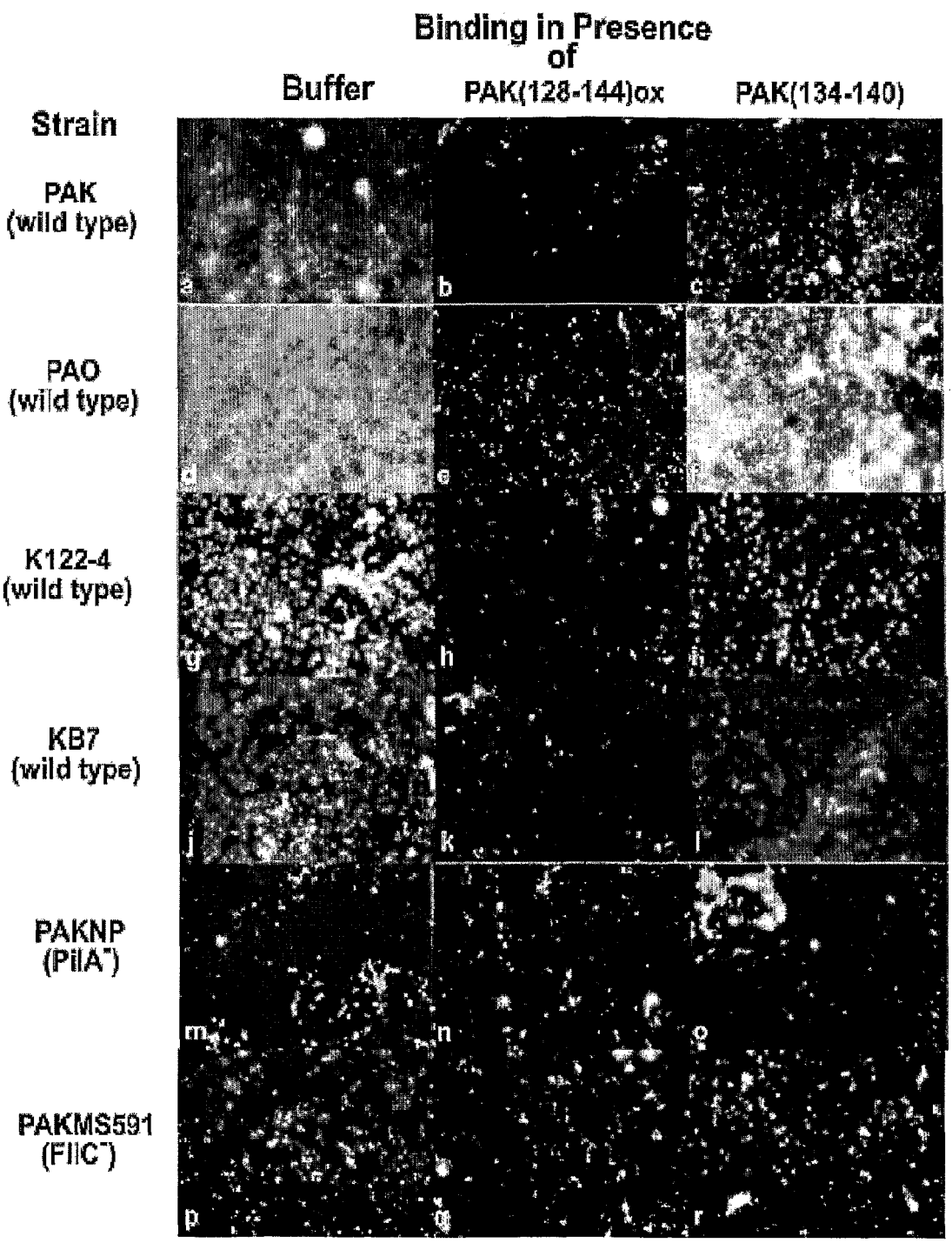
FIG. 2. Epifluorescence microscopy of stainless steel after binding of *P. aeruginosa* strains PAK (panels a, b, and c), PAO (panels d, e, and f), K122-4 (panels g, h, and i), KB7 (panels j, k, and l), PAKNP (panels m, n, and o) and PAKMS591 (panels p, q, and r). Viable cells were allowed to incubate directly (panels a, d, g, j, m, and p) with a stainless steel grade 304 surface for 60 min at 37° C. and washed 5 times with 10 mM PBS pH 7.4 containing 0.05% BSA. The cells were then stained using acrydine orange and a 40× objective field was photographed with a Leitz Laborlux microscope equipped with epifluorescent illumination and a Wild automatic exposure 35 mm camera system. Note that bound *Pseudomonas* cells are stained orange while green fluorescence indicates non-specific interaction of the fluorochrome with the surface. *P. aeruginosa* strains PAK, PAO, K122-4, KB7, PAKNP, and PAKMS591 were incubated with the synthetic peptide PAK (128-144d)ox (panels b, e, h, k, n, and q respectively) or with synthetic peptide PAK(134-140) (panels c, f, i, l, o, and r respectively). Note that PAK(128-144)ox reduced the binding to steel of strains PAK, PAO, K122-4, KB7 and PAKMS591 but did not reduce the binding of strain PAKNP. PAK(134-140) did not inhibit the binding of any strain to the steel surface.

While the involvement of type IV pili in biofilm formation on abiotic surfaces has been well documented (O'Toole and Kolter, 1998; Klausen et al., 2003), the molecular basis for that involvement has not been firmly established. Therefore, we investigated the ability of *P. aeruginosa* wild-type strains PAK, PAO, K122-4, and KB7, which display considerable differences in their pilin sequences, to bind to stainless steel (FIGS. 1-*a, b*). *P. aeruginosa* pilins are characterized by a highly conserved N-terminal α-helix and a semi-conserved C-terminal disulfide loop region but display minimal sequence similarity through the bulk of the protein (FIG. 1-*a*). However, structural studies indicate that *P. aeruginosa* pilins are strikingly similar (FIG. 1-*b*) (Hazes et al., 2000; Craig et al., 2003; and Audette et al., 2004). *P. aeruginosa* strains PAK, PAO, K122-4, and KB7 were observed to rapidly bind to stainless steel surfaces (FIGS. 2-*a, d, g*, and *j*), in agreement with previous results (Stanley, 1983; VanHaecke et al., 1990). Strains PAO and PAK bound more significantly to stainless steel than either K122-4 or KB7 (FIGS. 2-*a, d, g*, and *j*). *P. aeruginosa* strain MS591 (Starnback et al., 1992) a fliC$^-$ non-flagellated mutant of PAK, was observed to bind at considerably reduced levels compared to the parental PAK strain (FIGS. 2-a, and p). P. aeruginosa strain PAKNP, a non-piliated pilA⁻ deficient mutant of PAK (Saiman et al., 1990), did not bind to steel surfaces (FIG. 2-m), indicating that P. aeruginosa adherence to stainless steel is mediated by type IV pili. To further investigate the initial colonization of stainless steel, the binding kinetics of PAK cells and pili to steel was examined in a quantitative manner employing viable biotinylated cells and purified biotinylated PAK pili. PAK cells (FIG. 3a, FIG. 4), and purified PAK pili (FIG. 3b) were observed to bind to steel surfaces in a saturable, concentration dependent manner while PAKNP biotinylated cells (FIG. 3a, FIG. 4) did not bind appreciably to the steel surface. Biotinylation had no effect on the ability of the purified pili to bind stainless steel as identical binding kinetics were observed with native pili when anti-PAK pili antibodies were utilized to quantitate binding (data not shown). Furthermore, addition of low concentrations of purified PAK pili competitively inhibited the binding of biotinylated PAK cells to steel (FIG. 3c). Since the length of PAK pili is not known, the molarity of the pili cannot be determined (van Schaik et al., 2005).

We established that P. aeruginosa stained with acridine orange were readily visualized by epifluorescence microscopy following binding to stainless steel (FIG. 1-d). P. aeruginosa cells were visualized as fluorescent orange rods bound to areas of the steel that fluoresced green either through non-specific interaction of the fluorochrome with grain boundary regions or due to non-specific interaction of the fluorochrome with organic material that interacted with the grain boundaries in the steel. Green fluorescent material primarily associated with grain boundaries in the steel was observed in both strains PAK and PAKNP (FIGS. 1-d, e). In confirmation of these results, Pseudomonas sp. has recently been shown to colonize preferentially with grain boundaries (Sreekumari et al., 2001).

Effect of Flagella and Type IV Pili Mutations on Binding to Steel

Figure 4:
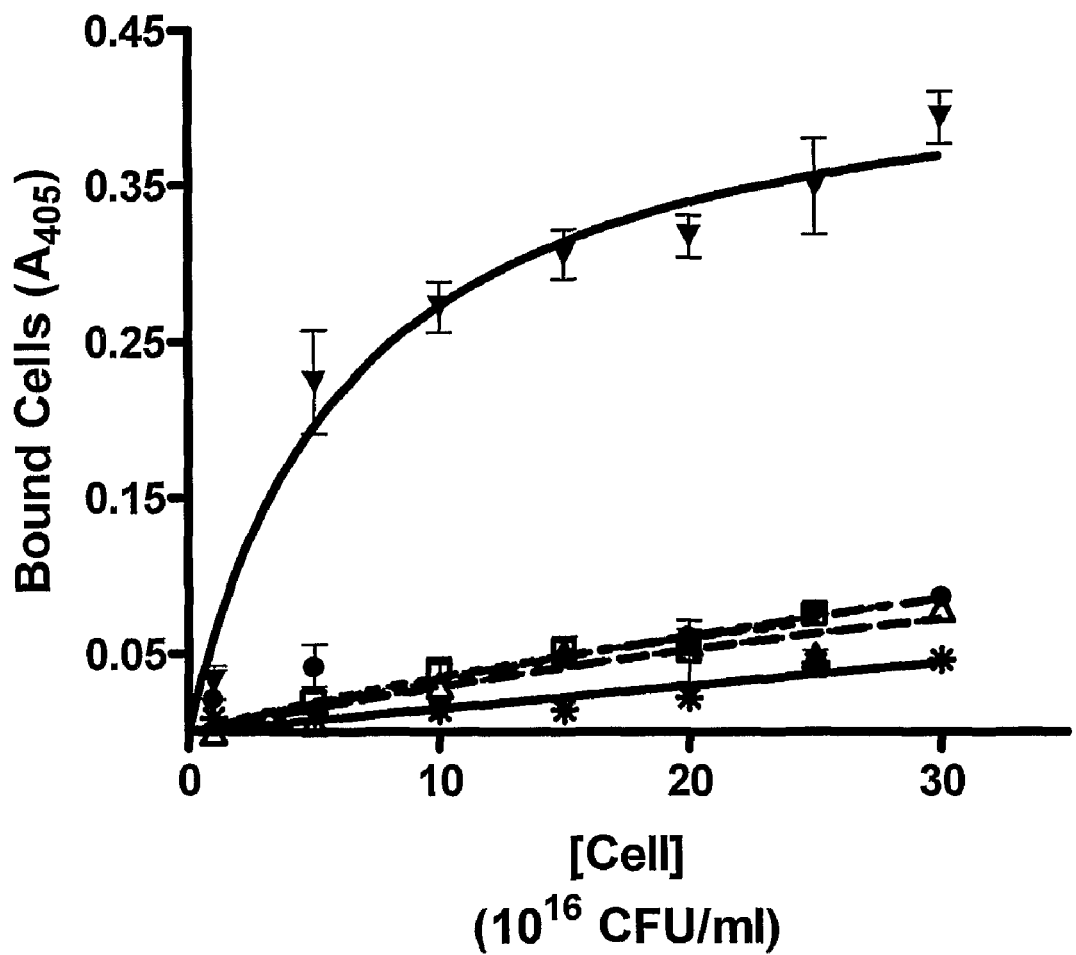
FIG. 4. Binding of biotinylated viable cells of *P. aeruginosa* strains PAKwt (▼), PAKMS591 a FliC⁻ strain (Δ), PAKΩB a PilB⁻ strain (●), PAKΩD a PilD⁻ strain (□), and PAKNP a PilA⁻ strain, (✳) binding to stainless steel. The quantity of PAK cells bound to the stainless steel surface area was determined by measuring the amount of biotin bound to the stainless steel surface employing a modified ELISA with streptavidin-HRP and utilizing ABTS as a substrate.

Previous studies using P. aeruginosa FilC⁻ and PilB⁻ strains have established the importance of flagella and type IV pili during the initiation and development of biofilms on abiotic surfaces in static cultures (O'Toole and Kolter, 1998). To confirm our qualtitative microscopic examination a quantitative analysis of adherence to steel was preformed. The binding of PAK-BΩ (PilB⁻ mutant), a strain that does not assemble pili but does express PilA (Koga et al., 1993), to steel was compromised relative to wild-type and equivalent adherence to that observed for PAKNP and PAKMS591 (FIG. 4). ELISA evidence indicates that PAKMS591 has less surface exposed pili than does the PAK wild-type strain (data not shown). Strain PAK-DΩ (pilD⁻ mutant) which lacks the prepilin peptidase and therefore does not express surface exposed PilA (Koga et al., 1993) or functional type IV pili, bound roughly equivalent to mutant strains (PAKNP, PAKMS591, and PAK-BΩ) (FIG. 4). Although the binding curves differ slightly between mutant strains, all pili deficient strains (PAKNP, PAK-BΩ, and PAK-DΩ), and PAKMS591, bound significantly less than wild-type (FIG. 4). These results indicate that any mutation which abolishes the production of functional pili also reduces the ability to bind stainless steel.

Antibody Inhibition Studies

Figure 5:
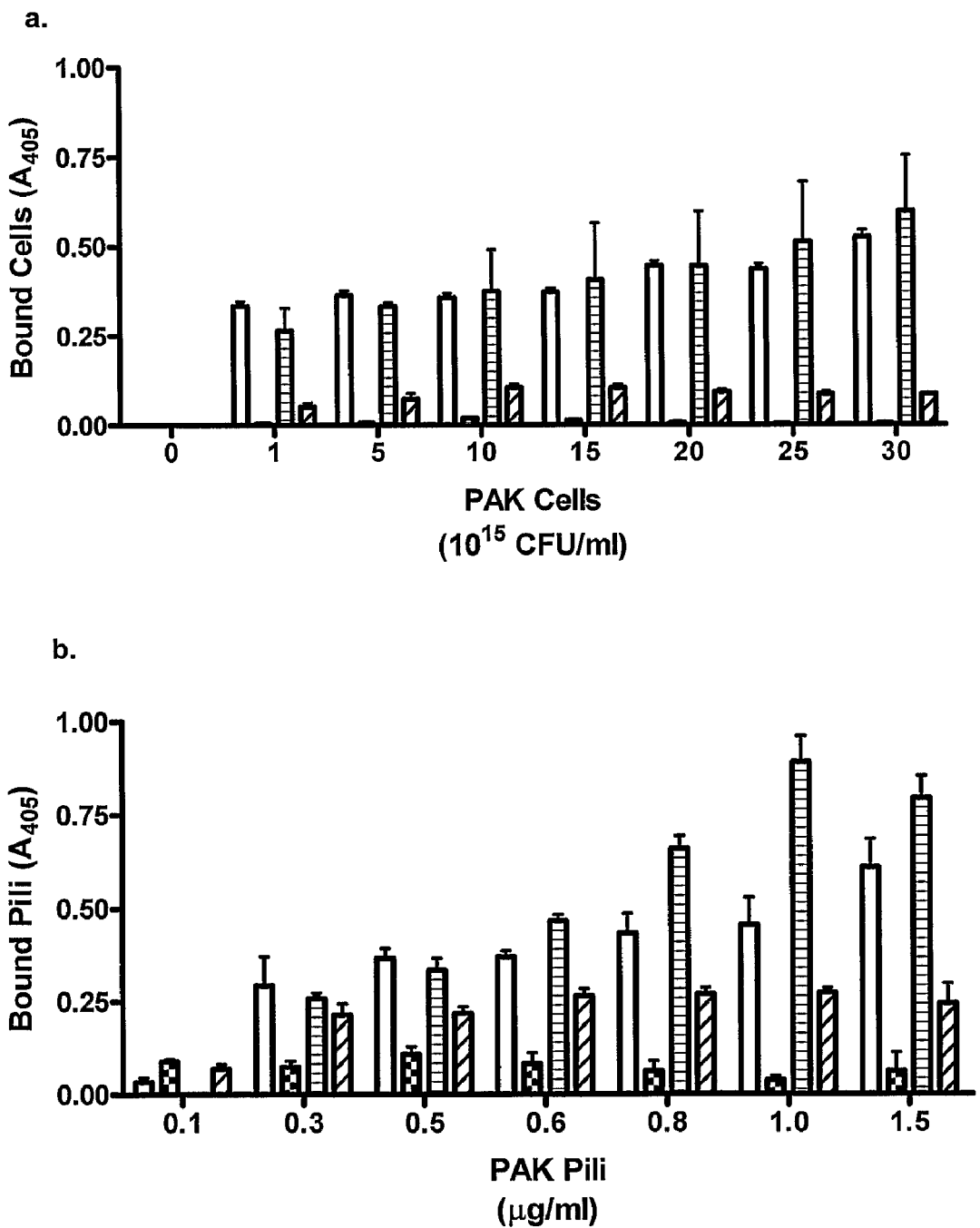
FIG. 5. (a) Antibody inhibition of the binding of viable biotinylated PAKwt cells to stainless steel relative to PAKwt cells in buffer (▭) or exposed to rabbit pre-immune antisera (▭). Antibodies utilized include rabbit polyclonal anti-PAK pili antisera (▭), and murine monoclonal antibody PK99H (▭) all of which are specific for PAK pili.
(b) Antibody inhibition of the binding of biotinylated PAK pili to stainless steel relative to PAK pili in buffer (▭) or exposed to rabbit pre-immune antisera (▭) Antibodies utilized include rabbit polyclonal anti-PAK pili antisera (▭) and murine monoclonal antibody PK99H (▭) all of which are specific for PAK pili.

Addition of rabbit polyclonal anti-PAK pili antibodies (Lee et al, 1989) but not rabbit pre-immune serum strongly inhibited the binding of biotinylated PAK cells and pili (FIG. 5) to steel in a dose-dependent manner. These data indicate that the type IV pili mediates binding. Murine monoclonal antibody PK99H, that recognizes PAK PilA residues 134-140 exposed at the tip of the pilus (Lee et al., 1994; Wong et al., 1992), significantly inhibited the binding of PAK cells and pili to steel (FIG. 5). The inhibition of PAK binding to stainless steel by PK99H suggests that the C-terminal di-sulfide loop region of pilin, which contains an epithelial cell binding domain, may also function in mediating attachment to steel surfaces.

Synthetic Peptide Inhibition of Binding to Steel

Figure 6:
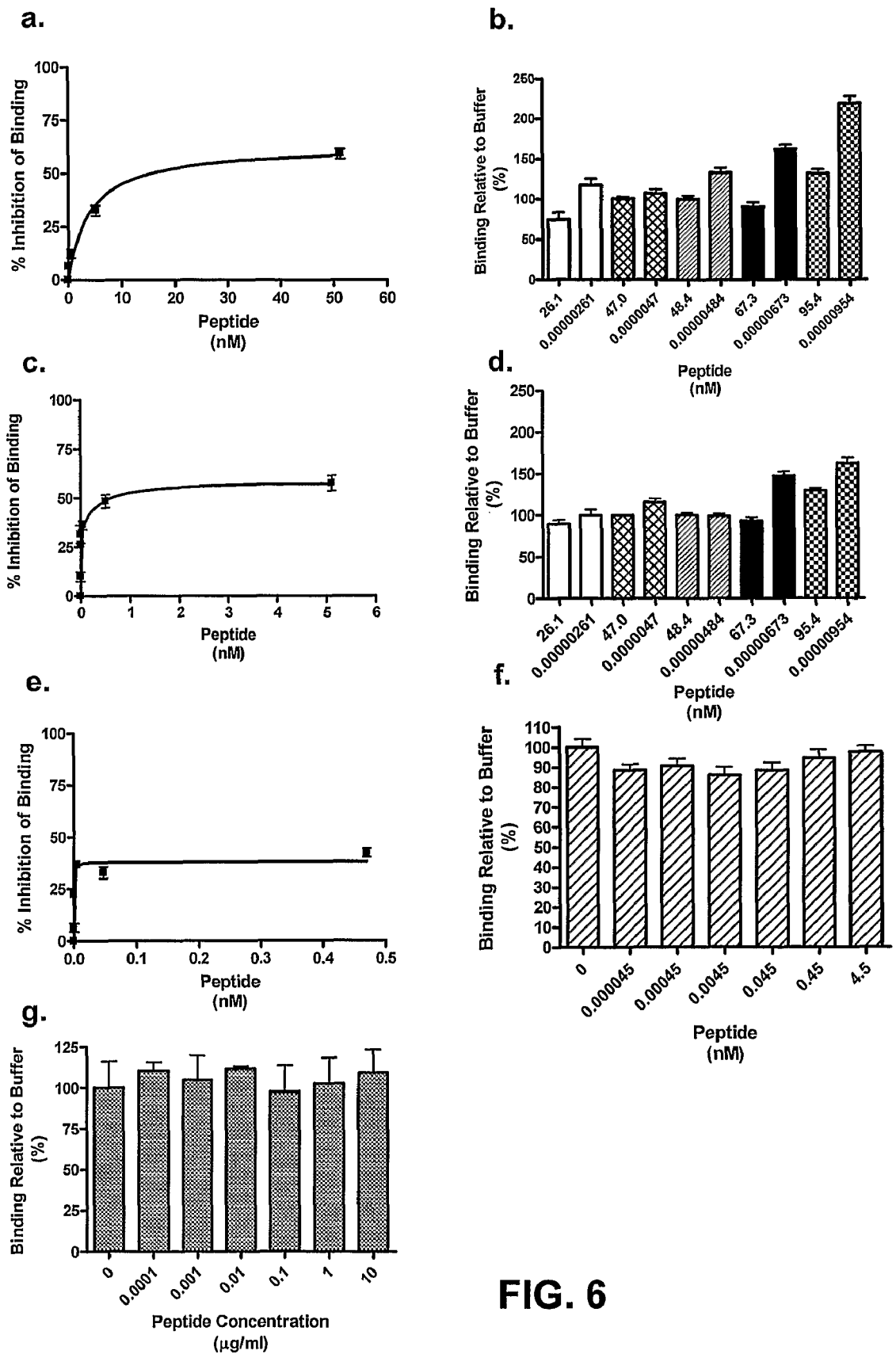
FIG. 6. (a) Competitive inhibition of biotinylated PAKwt cell binding to stainless steel by the synthetic peptide PAK (128-144)ox, the PilA receptor binding domain that binds to human respiratory epithelial cells. The apparent $K_i$ of the peptide inhibition of PAKwt binding to steel is ~4 nM as determined by Prism 4 curve fitting. (b) Bar graph of the effect of various synthetic peptides on the binding of biotinylated PAKwt cells to stainless steel. Synthetic peptides consisting of the PAK PilA sequences PAK(22-52) (▭) a portion of the N-terminal α-helix which is buried in the pilus fiber, PAK(117-125) (▭) a solvent exposed sequence of PilA located N-terminally to the receptor binding domain, and PAK(134-140) (▭) a sequence from the PilA receptor binding domain that has low affinity for mucosal cell surface receptors. Two scrambled peptide sequences were utilized as further controls, PAO(128-144)ox_Scrambled (▭), a PAO PilA receptor binding domain scrambled sequence that retains the intra-chain di-sulfide bond and PAO(128-144) C129A/C142A_Scrambled (▭) a linear variant of the initial scrambled sequence where the two cysteine residues have been replaced by alanine residues. See Table 1 for a list of sequences. Note that the control peptides do not inhibit cell binding to steel even at high concentrations. Indeed, PAK (117-125) appears to enhance cell binding to steel rather than inhibiting the binding function. (c) Competitive inhibition of biotinylated PAK pili binding to stainless steel by the synthetic peptide PAK(128-144)ox, the PilA receptor binding domain that binds to human respiratory epithelial cells. The apparent $K_i$ of the peptide inhibition of PAK pilus binding to steel is ~0.2 nM as determined by Prism 4 curve fitting. (d) Bar graph of the effect of various synthetic peptides on the binding of biotinylated PAK pili to stainless steel. Synthetic peptides and symbols are as for FIG. 5-b. Note that the control peptides do not inhibit the binding of pili to steel even at high concentrations. Indeed, PAK(117-125) appears to enhance the binding of pili to steel rather than inhibiting binding. (e) Competitive inhibition of biotinylated PAKwt cell binding to stainless steel by the synthetic peptide PAO(128-144)ox, the PilA receptor binding domain that binds to human respiratory epithelial cells. (f) Bar graph of the effect of PAO(128-144) T130I (▭) on the binding of biotinylated PAK pili to stainless steel. Note that the control peptides do not inhibit the binding of pili to steel even at high concentrations. (g) Bar graph of the effect of trypsinized peptide (▭) on the binding of biotinylated PAK pili to stainless steel. Note that the control peptides do not inhibit the binding of pili to steel even at high concentrations.

Antibody inhibition assays suggested that the cellular receptor binding domain of the pilus may also mediate binding to stainless steel. Therefore, competitive binding assays were utilized to test the ability of the C-terminal receptor binding domain to inhibit adherence of P. aeruginosa to steel. Previous studies demonstrated that the native C-terminal receptor binding domain (PAK(128-144)ox) mediates binding to GalNAc-β-D-Gal containing glycoconjugates (Sheth et al., 1994). The PAK pilin receptor binding domain (PAK(128-144)ox) inhibited the binding of both PAK wild-type cells and PAK pili to steel surfaces with apparent $K_i$'s of ~4 nM and ~0.2 nM respectively (FIGS. 6-a, and c). PAK(128-144)ox also inhibited the binding of PAKMS591 (compare FIG. 2-p with FIG. 2-q) but had no effect on the binding of PAKNP (compare FIG. 2-m and FIG. 2-n). The peptide PAK (134-140), which constitutes a portion of the receptor binding domain, and has been demonstrated to bind with low affinity to respiratory epithelial cells (Yu et al., 1996), did not inhibit binding of PAK wild-type cells or PAK pili to steel surfaces, even at the exceptionally high peptide concentration of 100 μg/ml (FIGS. 6-b, and d), nor did it inhibit the binding of strains PAO, K122-4 or KB7, in contrast to peptide PAK(128-144)ox (FIG. 2). In addition, neither PAK(22-52), a peptide derived from the N-terminal α-helix (residues 1-58) which should be buried in the native pilus fiber nor PAK(117-125), a peptide consisting of a portion of β-strands 3 and 4 which models of the pilus fiber suggest will be displayed on the fiber surface (Hazes et al., 2000) (see Table 1 for peptide sequences and FIG. 1-b) had any effect, even at high concentrations, on the binding of PAK wild-type cells or PAK pili to steel surfaces (FIGS. 6-b, d), indicating that these regions do not participate in pilus-mediated binding.

To determine whether the ability to interact with steel surfaces was a general attribute of the C-terminal receptor binding domain or a specific property of the PAK receptor binding domain, the ability of the PAO receptor binding domain to inhibit binding was examined. The synthetic PAO receptor binding domain, PAO(128-144)ox was observed to inhibit pilus-mediated binding to stainless steel in a similar manner to the native PAK peptide (FIG. 6-e). To further confirm the specific nature of the receptor binding domain's interaction with steel surfaces two additional control peptides, a scrambled PAO receptor binding domain PAO(128-144)ox_Scrambled, and a linear variant of that sequence where the two cysteine residues have been replaced by alanine residues to eliminate the di-sulfide bridge, PAO(128-144)C129A/C142A_Scrambled, were utilized to assess the relative importance of sequence versus amino acid composition. Neither scrambled sequence was able to inhibit binding of PAK wild-type cells or PAK pili to steel surfaces, even at very high peptide concentrations (FIGS. 6-b, and d). As a further control, peptides obtained through the trypsinization of bovine serum albumin were utilized to confirm that the inhibition of binding was sequence specific and not a common property of peptides. No inhibition of adherence was observed for either PAK whole cells (data not shown) or PAK pili even at high peptide concentrations (FIG. 6-g). A PAO receptor binding domain mutant, PAO(128-144)oxT130I which has high affinity for human buccal epithelial cells (FIG.

Figure 7:
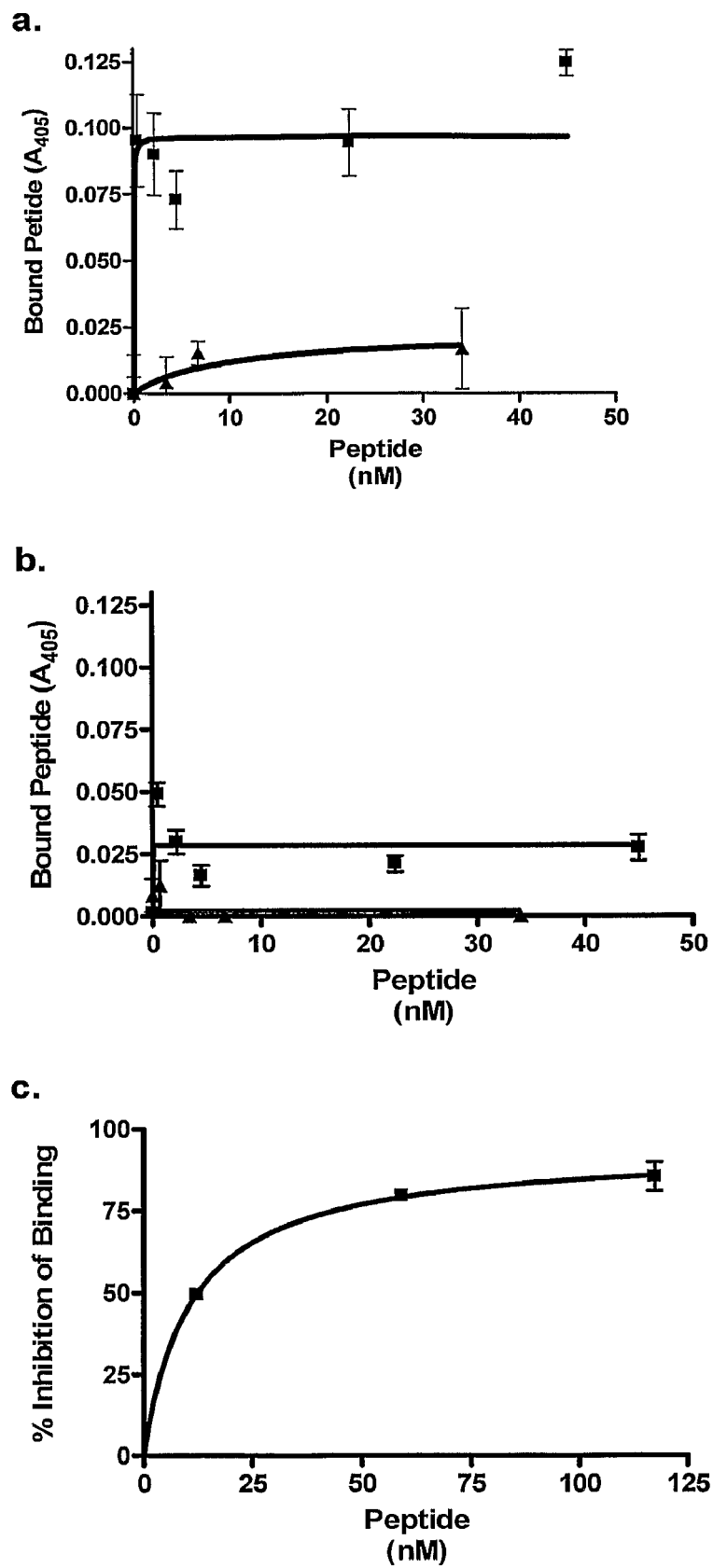
FIG. 7. (a) Binding of PAK(128-144)ox (■) and PAK(134-140) (▲) to stainless steel as determined by a direct immunoassay employing murine monoclonal antibody PK99H. PK99H binds with high affinity to both of these peptides (Doig et al., 1990; Wong et al., 1992) even when the peptides are bound to receptors (Irvin et al., 1989; Yu et al, 1996). Note that PAK(128-144)ox binds with high affinity to steel while PAK(134-140) binds only slightly at very high concentrations. (b) Binding of PAK(128-144)ox (■) and PAK(134-140) (▲) to stainless steel as determined by a direct immunoassay employing biotinylated peptide. Note that PAK(128-144)ox binds with high affinity to steel while PAK(134-140) binds only slightly at very high concentrations. (c) Competition assay using immobilized buccal epithelial cells (BECs) and wild-type PAO with PAO(128-144)T130I peptide in increasing concentrations.

7-c) was unable to inhibit *P. aeruginosa* whole cells or pili adherence to steel (FIG. 6). This indicates that the amino acid sequence of this peptide is important for adherence to stainless steel. To further determine whether the receptor binding domain inhibited binding to steel by a competitive mechanism or by interacting with *P. aeruginosa* cells or pili, the ability of PAK(128-144)ox to bind to stainless steel was determined using the monoclonal antibody PK99H as a probe of peptide binding to steel (PK99H has been demonstrated to bind to both PAK(128-144)ox and PAK(134-140) when these peptides are bound to a cell surface receptor) (Yu et al., 1996; Irvin et al., 1989). PAK(128-144)ox bound with high affinity to stainless steel while PAK(134-140) bound only marginally to the steel surface at very high concentrations (FIGS. 7-a, b).

As *P. aeruginosa* strains vary considerably in their ability to bind to steel surfaces (FIGS. 2-a, d, g, and j) we sought to determine whether the PAK pilin receptor binding domain, PAK(128-144)ox, could inhibit the binding of other *P. aeruginosa* strains. Utilizing microscopy, we found that at very low concentrations (51 nM), PAK(128-144)ox substantially inhibits the binding of strains PAO, K122-4, and KB7 (compare figures FIGS. 2-d, g, and j with figures FIGS. 2-e, h, and k) while very high concentrations (100 µg/ml) of PAK (134-140) have a minimal effect on binding to steel (compare figures FIGS. 2-a, d, g, and j with figures FIGS. 2-c, f, i, and l). The pilin receptor binding domain sequences of strains PAK, PAO, K122-4 and KB7 vary substantially (FIGS. 1-a, and b, and Table 1) but all these receptor binding domains display a conserved antigenic epitope and compete for epithelial cell surface receptors (Sheth et al, 1995).

TABLE 1

Synthetic peptides and peptide sequences employed or referred to in this study.

| Peptide | Sequence |
| --- | --- |
| PAK(128-144)ox (SEQ ID NO: 3) | Ac-K-C-T-S-D-Q-D-E-Q-F-I-P-K-G-C-S-K-OH |
| PAK(134-140) (SEQ ID NO: 8) | Ac-D-E-Q-F-I-P-K-amide |
| PAK(117-125) (SEQ ID NO: 9) | Ac-T-L-T-R-T-A-A-D-G-OH |
| PAK(22-52) (SEQ ID NO: 10) | Ac-P-Q-Y-Q-N-Y-V-A-R-S-E-G-A-S-A-L-A-S-V-N-P-L-K-T-T-V-E-E-A-D-P-OH |
| PAO(128-144)$_{ox\_}$ Scrambled (SEQ ID NO: 11) | Ac-N-C-P-D-F-D-P-T-K-K-G-M-Q-A-C-T-S-OH |
| PAO(128-144)C129A/ C142A_Scrambled (SEQ ID NO: 12) | Ac-N-A-P-D-F-D-P-T-K-K-G-M-Q-A-A-T-S-OH |
| PAK(128-144)ox (SEQ ID NO: 3) | Ac-K-C-T-S-D-Q-D-E-Q-F-I-P-K-G-C-S-K-OH |
| PAO(128-144)ox (SEQ ID NO: 4) | Ac-A-C-K-S-T-Q-D-P-M-F-T-P-K-G-C-D-N-OH |
| PAO(128-144)oxK130I (SEQ ID NO: 13) | Ac-A-C-I-S-T-Q-D-P-M-F-T-P-K-G-C-D-N-OH |

Peptides were synthesized by solid phase and are N-α-acetylated with a free carboxyl except for PAK(134-140) which was synthesized as the N-α-acetylated amide peptide due to its short length. Peptides with a formed di-sulfide bridge between cysteine 129 and 142 are identified by an ox.

Binding to Other Abiotic Surfaces

Figure 8:
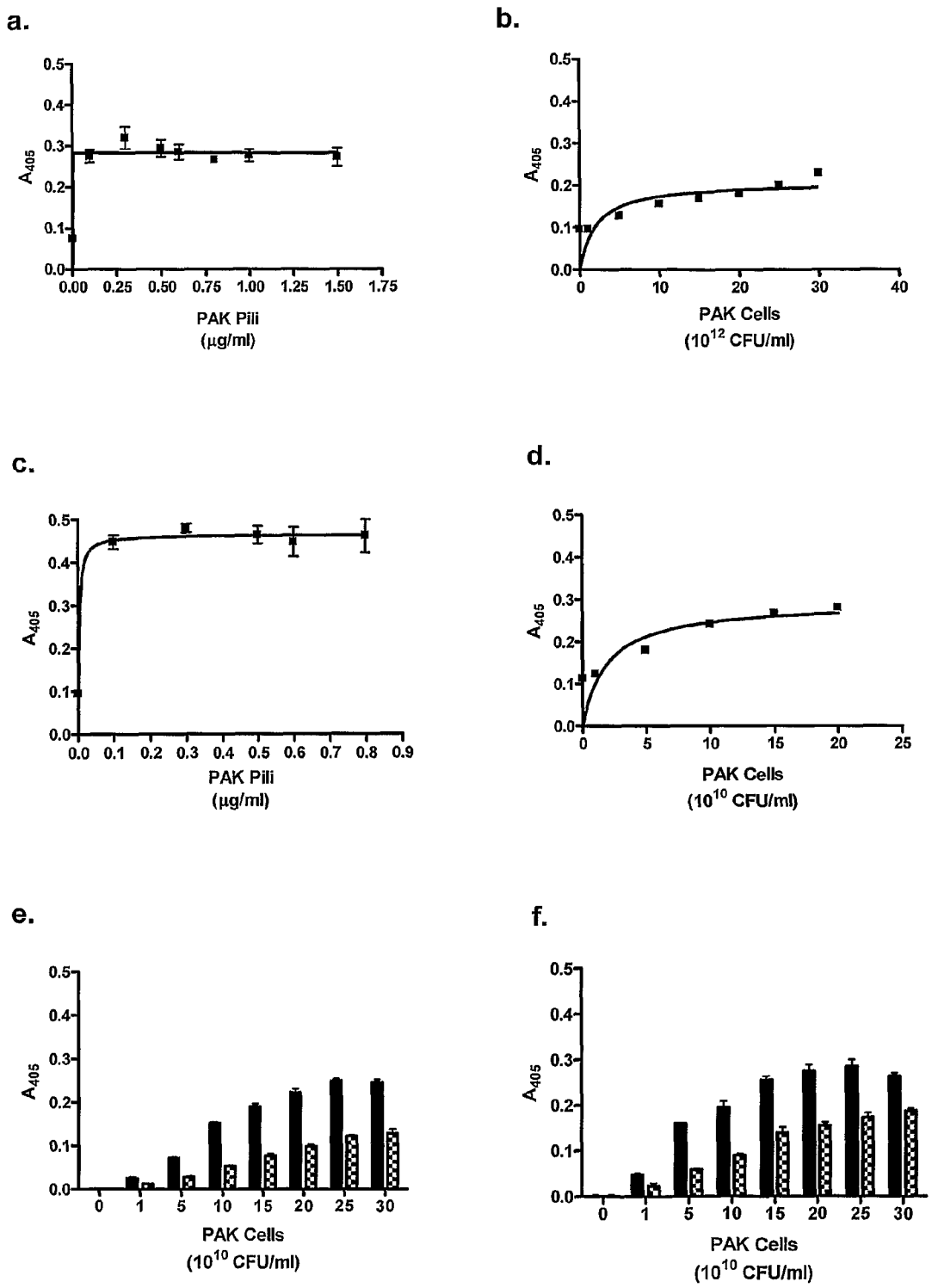
FIG. 8. (a) Binding of biotinylated PAK pili (■) to polystyrene plastic. Biotinylated pili were washed and suspended in 10 mM PBS pH 7.4, and allowed to bind to polystyrene for 60 min at 37° C. (b) Binding of biotinylated viable whole cells of *P. aeruginosa* strain K (PAK) (■) to polystyrene at cell densities of $10^{12}$ CFU/ml. The quantity of PAK cells bound to the polystyrene surface area was determined by measuring the amount of biotin bound to the polystyrene surface employing a modified ELISA with streptavidin-HRP and utilizing ABTS as a substrate. (c) Binding of biotinylated PAK pili (■) to polyvinylchloride plastic. (d) Binding of biotinylated viable whole cells of *P. aeruginosa* strain K (PAK) (■) to polyvinylchloride at cell densities of $10^{12}$ CFU/ml. (e, f) Antibody inhibition of the binding of viable biotinylated PAKwt cells to polyvinylchloride (e) or polystyrene (f) relative to PAKwt cells in buffer (▭) or exposed to murine monoclonal antibody PK99H (■).

As type IV pili have been implicated in biofilm formation on polystyrene and polyvinylchloride surfaces, we sought to determine if the C-terminal receptor binding domain may function to mediate attachment to a variety of abiotic surfaces. PAK whole cells and pili were found to bind in a concentration dependent and saturable manner to both polyvinylchloride and polystyrene plates (FIGS. 8-a, b, c, and d). The murine monoclonal antibody PK99H significantly inhibited binding to both polyvinyl chloride and polystyrene surfaces (FIG. 8-e, and f). These data indicate that type IV pili mediate binding to these plastic surfaces which may be dependant on the C-terminal receptor binding domain.

The aggressive colonization of stainless steel surfaces, apart from being of enormous industrial significance, is also of medical relevance; *P. aeruginosa* infections are prevalent in burn units where large stainless steel tubs, known as hydrotherapy units, are often used to treat patients with severe burns (Tredget et al., 1992). Tredget et al. (1992) have demonstrated a significant decrease in *P. aeruginosa* infection rates in burn units where stainless steel hydrotherapy units were removed. Biofilm formation on stainless steel and other substrata, as a function of physical and chemical modifications, has been widely investigated (Arnold et al., 2004; Balazs et al., 2004; Groessner-Schreiber et al., 2004; Lomander et al., 2004). Rough stainless steel surfaces more readily develop biofilms compared with smooth, or electropolished, steel (Characklis et al. 1990; VanHaecke et al. 1990; Bagge et al., 2001; Balazs et al., 2004; Lomander et al., 2004). We sought to clarify the role of the *P. aeruginosa* type IV pilus in the initial colonization of abiotic surfaces, particularly with stainless steel given the classic genetic evidence that flagella are more likely responsible for the initial stages of *P. aeruginosa* biofilm formation (O'Toole and Kolter, 1998).

Figure 3:
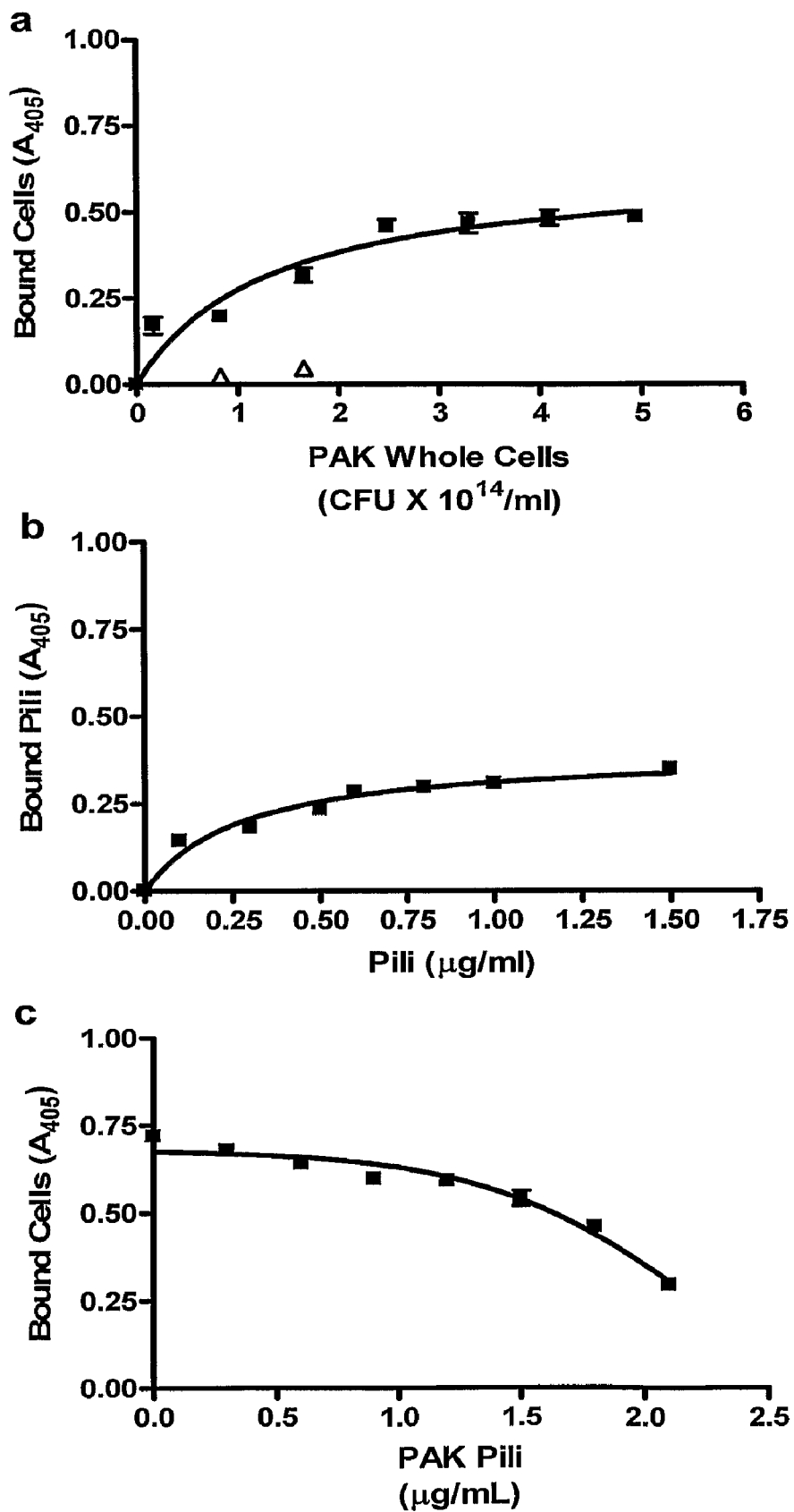
FIG. 3. (a) Binding of biotinylated viable whole cells of *P. aeruginosa* strain K (PAK) (■) and a pilin deficient strain PAKNP (Δ) to stainless steel at cell densities of $10^{14}$ CFU/ml. The quantity of PAK cells bound to the stainless steel surface area was determined by measuring the amount of biotin bound to the stainless steel surface employing a modified ELISA with streptavidin-HRP and utilizing ABTS as a substrate. The symbols and bars in this and subsequent figures report the mean±SEM (experiments were duplicated with individual studies employing at least 6 replicates). (b) Binding of biotinylated PAK pili to stainless steel. Biotinylated pili were washed and suspended in 10 mM PBS pH 7.4, and allowed to bind to stainless steel for 60 min at 37° C. (c) Competitive inhibition of viable biotinylated-PAK whole cell binding to stainless steel surfaces by purified homologous unlabelled pili. Pili and bacteria were mixed and then directly added to the stainless steel surface.

We demonstrated that the initial binding of *P. aeruginosa* to stainless steel is concentration dependent and exhibits classical saturation kinetics (FIG. 3). *P. aeruginosa* pili clearly play a major role in mediating whole, cell binding to stainless steel as (1) pili-deficient strains are unable to adhere, (2) pili bind to steel in a concentration-dependent, saturable manner, and (3) pili competitively inhibit whole cell binding in a direct competition assay (FIG. 3).

Although Wozniak et al. (2003) demonstrated that alginate, the primary exopolysaccharide of *P. aeruginosa*, did not have a significant effect on the initial binding of *Pseudomonas* to abiotic surfaces, we have demonstrated that type IV pili are involved in the initial adherence. Therefore, while extracellular polysaccharide has long been proposed to play a major role in mature biofilms (Stoodley et al., 2002), type IV pili protein subunits provide the initial attachment to abiotic surfaces (FIGS. 2 and 3). Evidence of an initial involvement of protein in biofilm formation on copper surfaces has been reported previously (Bremer and Geesey, 1991). Interestingly, a variety of proteins have the ability to mediate tight interactions with abiotic surfaces, including the Mytilus edulis foot proteins which are capable of mediating interactions with a variety of abiotic surfaces including metals and plastics (Suci and Geesey, 2001). A direct role for protein in mediating interactions with an abiotic surface, particularly a metal surface, is thus not without precedent.

While O'Toole and Kolter (1998) found that flagella play a significant role in biofilm formation, we found that *P. aeruginosa* lacking flagella yet expressing pili were able to bind to steel (FIGS. 2 and 4). In addition, any strain lacking the ability to assemble functional pili were unable to bind (FIGS. 2 and 4). The difference between our findings and those of O'Toole and Kolter (1998) may reflect the ability of bound cells to remain surface attached and differentiate into a microcolony, and subsequently a biofilm, as our data only reports on events that occur within about 1 hour of a potential bacterial interaction with the surface.

To determine whether the C-terminal receptor binding domain of the pilus was responsible for adherence to stainless steel, as for BECs (Irvin et al., 1990; Schweizer et al., 1998), we employed monoclonal antibodies specific for residues in the C-terminal binding domain in a competitive inhibition assay. Monoclonal antibody PK99H recognizes residues 134-140 of PAK PilA (Wong et al., 1992), inhibits pilus mediated binding to respiratory epithelial cells (Irvin et al., 1989), and confers protection from challenge with strain PAK in a mouse infection model (Sheth et al., 1995). PK99H inhibited pilus-mediated binding to stainless steel, indicating that the pili C-terminal receptor binding domain, residues 128-144 of PAK PilA, specifically mediate the interaction with steel (FIG. 5).

To confirm that residues 128-144 were mediating the interaction between pili and steel a variety of synthetic peptides were used in competitive inhibition assays. Strikingly, PAK (128-144)ox effectively inhibits the adherence of heterologous *P. aeruginosa* strains to stainless steel even at low concentrations (FIGS. 2-*b, e, h*, and *k*) indicating that the ability to bind to steel through the C-terminal binding domain is conserved in all *P. aeruginosa* strains. The ability of the synthetic receptor binding domain, PAO(128-144)ox, to inhibit the binding of both PAK cells and pili to steel further supports our hypothesis that the C-terminal pilin receptor binding domain of the various pilins mediates binding to steel in addition to mediating binding to human respiratory epithelial cells.

Peptides with limited affinity for steel have been identified by phage display methodology and their affinity for steel has been correlated to their amino acid composition (Zuo et al., 2005). The interaction of the receptor binding domain with steel is not simply a function of the peptide amino acid composition as two scrambled sequences of the PAO receptor binding domain (one retaining the di-sulfide bridge and the other a linear variant where the two cysteine residues are replaced with alanine residues) failed to inhibit binding to steel (FIGS. 6-*b, d*). The PilA receptor binding domain binds to steel with high affinity in a sequence specific manner indicating that binding is likely dependent upon both the sequence and three dimensional structure of the peptide rather than the amino acid composition. The steel binding function is sequence specific as PAO(128-144)oxT130I failed to inhibit binding to steel even though the affinity of this peptide for human buccal epithelial cells was enhanced (compare FIG. 6-*f* with FIG. 7-*c*). This observation suggests that the ability to bind to steel and human epithelial cells can be differentiated, indeed, the short synthetic peptide PAK(134-140) which has previously been demonstrated to have a low affinity for human buccal epithelial cells (Yu et al., 1996) did not inhibit binding to steel (FIG. 2). These results indicate that the two binding functions are readily differentiated by a single point mutation, suggesting that the molecular basis of the interaction with steel and epithelial cells is quite distinct, although both are dependent on the C-terminal receptor binding domain.

As type IV pili have also been implicated in biofilm formation on plastic surfaces, the ability of the PilA receptor binding domain to mediate adherence to two widely used plastics, polyvinylchloride and polystyrene, was examined. Direct binding assays demonstrate that PAK whole cells and pili adhere to plastics in a concentration dependent and saturable manner (FIG. 8). As well, the monoclonal antibody PK99H was able to inhibit *P. aeruginosa* binding to both polyvinylchloride and polystyrene plates (FIG. 8). These data indicate that the C-terminal receptor binding domain is involved not only in adherence to stainless steel and buccal epithelial cells, but also to other abiotic substrates including plastics.

The PilA C-terminal receptor binding domain, displayed at the tip of the type IV pilus, mediates direct binding to both biotic and abiotic surfaces, although the pilus is able to bind both substrates the affinities differ by several orders of magnitude. However, as the single point mutation in the C-terminal receptor binding domain increased the affinity for BECs, it abolished the affinity for stainless steel. This supports our hypothesis that the receptor binding domain has retained sequence and structural elements required for adherence to a variety of surfaces. Therefore, we have determined that the C-terminal receptor binding domain is responsible for adherence to stainless steel, and although the sequence varies widely between strains, attachment via this C-terminal receptor binding domain is not strain specific.

In summary, the studies disclosed herein demonstrate that: 1) *P. aeruginosa* biofilm formation on stainless steel and other abiotic surfaces is initiated by the adherence of the bacterium to the steel surface; 2) *P. aeruginosa* adherence to steel and plastic surfaces is mediated by type IV pili and specifically involves the PilA receptor binding domain that is displayed at the tip of the pilus; and 3) the receptor binding domain mediates a specific high affinity, direct interaction with stainless steel and plastic surfaces. Based on the fact that the PAK (128-144)ox peptide not only binds to an abiotic surface with high affinity but also inhibits binding of other heterologous *P. aeruginosa* strain to the same surface and that the amino acid sequences in this region of the receptor binding domain is highly conserved among most strains of *P. aeruginosa*, it is predicted that a peptide of approximately 10 to 14 amino acids in length corresponding to the PilA receptor binding domain (e.g. PAK128-144) from any other strain of *Pseudomonas* would also be able to prevent or inhibit biofilm formation on a surface. Table 2 below provides candidate peptides useful for the inventive composition and method.

TABLE 2

Exemplary peptides useful to prevent or inhibit biofilm formation according to the inventive method.

| Peptide | Sequence |
|---|---|
| PAK(128-144) | K-C-T-S-D-Q-D-E-Q-F-I-P-K-G-C-S-K (SEQ ID NO: 3) |
| PAO(128-144) | A-C-K-S-T-Q-D-P-M-F-T-P-K-G-C-D-N (SEQ ID NO: 4) |
| KB7(128-144) | S-C-A-T-T-V-D-A-K-F-R-P-N-G-C-T-D (SEQ ID NO: 5) |
| K122-4(128-144) | A-C-T-S-N-A-D-N-K-Y-L-P-K-T-C-Q-T (SEQ ID NO: 6) |
| CD4(128-144) | T-C-T-S-T-Q-E-E-M-F-I-P-K-G-C-N-K (SEQ ID NO: 7) |
| Pa1244 | N-C-K-I-T-K-T-P-T-A-W-K-P-N-Y-A-P-A-N-C-P-K-S (SEQ ID NO: 14) |
| Pa5658 | T-C-A-T-S-G-S-P-A-N-W-K-A-N-Y-A-P-A-N-C-P-K-S (SEQ ID NO:15) |

TABLE 2-continued

Exemplary peptides useful to prevent
or inhibit biofilm formation according
to the inventive method.

| Peptide | Sequence |
|---|---|
| Pa5235 | S-C-A-T-T-V-D-A-K-F-R-P-N-G-C-T-D (SEQ ID NO: 16) |
| G7-G9 | G-C-A-S-D-S-N-A-V-S-S-G-T-D-R-N-M-P-A-L-T-A-G-T-L-P-A-R-F-A-P-S-E-C-R (SEQ ID NO: 17) |
| Pa5196 | A-C-G-N-A-S-I-D-G-F-A-G-T-G-T-T-I-D-A-K-Y-L-P-N-A-C-K-P (SEQ ID NO: 18) |
| Pa110594 | A-C-T-S-A-S-N-A-T-A-T-A-Q-F-T-G-M-A-A-G-S-V-P-Q-E-F-A-P-A-Q-C-R (SEQ ID NO: 19) |

The above are examples of pilA C-terminal domains representing class I to V as defined by Kus, J. V., Tullis, E., Cvitkovitch, D. G. & Burrows, L. L. (2004). *Microbiology* 150, 1315-1326.

Given that 1) all *P. aeruginosa* strains express a type IV pilus, that 2) they are capable of generating biofilms on abiotic surfaces, that 3) that all *P. aeruginosa* type IV pilins display a conserved antigenic epitope with the C-terminal disulfide loop, that 4) the PAK C-terminal peptide sequence has been effective in preventing biofilm formation of heterologous strains expressing pilins with varied C-terminal disulfide loop sequences, and that 5) the synthetic peptide PAK (128-144)ox binds to steel and inhibits biofilm formation by both homologous and heterologous strains, it is predicted that all the C-terminal disulfide sequences of all *P. aeruginosa* strains mediate binding to abiotic surfaces. It is further predicted that a peptide derived from this C-terminal disulfide sequences of any *P. aeruginosa* strain will be able to prevent or inhibit biofilm formation by either homologous or heterologous strain of *Pseudomonas*.

The sequences of *Pseudomonas aeruginosa* pilin involved in the binding to the steel surface are compared as shown below in Tables 3 and 4. These data came from 165 different strains of clinical isolates of which 100 strains or 61% were of the PAK/PAO type. It is clear that certain residues are highly conserved, for example, C at 129, S/T at 131, D/E at 134, FN at 137, P at 139, K/N at 140 G/T at 141, and C at 142. As disclosed herein, certain residues in this region (128-144) are critical for binding to steel. For example, lysine at position 130 of PAO(128-144) was found to be important in steel binding since the peptide PAO(128-144)oxK130I did not bind to stainless steel. However, a single point mutation in the PAO(128-144)ox peptide sequence can significantly enhance binding to human respiratory epithelial cells by ~60 fold (PAO(128-144)ox has apparent Ki of ~12000 nM for inhibiting viable cell binding to human buccal epithelial cells while the peptide PAO(128-144)oxK130I has an apparent Ki of ~38 nM).

The fact that certain amino acid residues are highly conserved among the peptides compared below and that certain amino acid residues at a given position show high prevalence in a large number of *Pseudomonas* isolates indicates that any native peptide derived from the corresponding region (e.g. PAK128-144) of any *Pseudomonas* pilin, particularly those of any *P. aeruginosa* strain, would have the steel and/or plastic binding properties (i.e., high binding affinity to abiotic surfaces). It is further predicted that a synthetic peptide of approximately 10-14 amino acids, preferably about 14 amino acids in length, having certain representative conserved amino acids from one strain (e.g. PAK) combined with those from another strain (e.g. PAO) would also be useful to prevent or inhibit biofilm formation (e.g. K-C-T-S-T-Q-D-E-Q-F-I-P-K-G-C-S-K, SEQ ID NO:1). Based on the information shown in Tables 3 and 4, the inventive peptide can have a general core sequence, K/A/S/T-C-T/K/A-S/T-D/T/N-Q/V/A-D/E-E/P/A/N-Q/M/K-F/Y-I/T/R/L-P-K/N-G/T-C-S/D/T/Q/N-K/N/D/T (SEQ ID NO:2).

TABLE 3

PAK/PAO Type Strains of *Pseudomonas aeruginosa*[a]

| | Strains | | | | | | | | | |
|---|---|---|---|---|---|---|---|---|---|---|
| | PAK | | PAO | | KB7 | | K122-4 | | CD4 | Total[c] |
| Position | Residue | %[b] | Residue | % | Residue | % | Residue | % | Residue | % % |
| 128 | K | 17 | A[d] | 61 | S | 13 | A | | T | 9 100 |
| 129 | C | 100 | C | | C | | C | | C | 100 |
| 130 | T | 76 | K | 11 | A | 13 | T | | T | 100 |
| 131 | S | 85 | S | | T | 15 | S | | S | 100 |
| 132 | D | 17 | T | 33 | T | | N | 50 | T | 100 |
| 133 | Q | 37 | Q | | V | 13 | A | 50 | Q | 100 |
| 134 | D | 91 | D | | D | | D | | E | 9 100 |
| 135 | E | 24 | P | 11 | A | 13 | N | 50 | E | 98[e] |
| 136 | Q | 17 | M | 20 | K | 63 | K | | M | 100 |
| 137 | F | 50 | F | | F | | Y | 46 | F | 96[f] |
| 138 | I | 26 | T | 11 | R | 13 | L | 50 | I | 100 |
| 139 | P | 100 | P | | P | | P | | P | 100 |
| 140 | K | 87 | K | | N | 13 | K | | K | 100 |
| 141 | G | 50 | G | | G | | T | 50 | G | 100 |

TABLE 3-continued

PAK/PAO Type Strains of *Pseudomonas aeruginosa*[a]

| | Strains | | | | | | | | | |
|---|---|---|---|---|---|---|---|---|---|---|
| | PAK | | PAO | | KB7 | | K122-4 | | CD4 | Total[c] |
| Position | Residue | %[b] | Residue | % | Residue | % | Residue | % | Residue | % % |
| 142 | C | 100 | C | | C | | C | | C | 100 |
| 143 | S | 17 | D | 11 | T | 13 | Q | 50 | N | 7  98[g] |
| 144 | K | 19 | N | 11 | D | 15 | T | 50 | K | 95[e] |
| SEQ ID NOs | 3 | | 4 | | 5 | | 6 | | 7 | |

[a]PAK/PAO type strains represent 61% of 165 clinically isolated strains.
[b]Represents the % prevalence of this amino acid residue in this position from 100 clinically isolated PAK/PAO type strains.
[c]The amino acid residues found in this position in these five strains represent the percent prevalence of these residues in the 100 isolated PAK/PAO type strains, e.g. at position 128 the four different residues (K, A, S and T) found in these five strains represent 100% of the residues found at this position among all PAK/PAO type clinical isolates.
[d]A boldface residues denotes a difference from the PAK sequence.
[e]The prevalence in percent is only for the four most frequent residues at this position.
[f]Histidine (H) occurred at 4%.
[g]These five residues account for 98% of observed PAK/PAO type clinical isolates.

TABLE 4

Sequences of the C-Terminal Region of Five *Pseudomonas aeruginosa* Pilin Strains

| Strain | Amino Acid Sequence |
|---|---|
| PAK | K - C - T - S - D - Q - D - E - Q - E - I - P - K - G - C - S - K |
| PAO | A - C - K - S - T - Q - D - P - M - E - T - P - K - G - C - D - N |
| KB7 | S - C - A - T - T - V - D - A - K - E - R - P - N - G - C - T - D |
| K122-4 | A - C - T - S - N - A - D - N - K - V - L - P - K - T - C - Q - T |
| CD4 | T - C - T - S - T - Q - E - E - M - E - I - P - K - G - C - N - K |

*Open boxes are identical among these five strains.
Shaded boxes denote conservative substitutions at the positions indicated. The sequence identifiers for the five sequences in the table are:
PAK (SEQ ID NO: 3), PAO (SEQ ID NO: 4), KB7 (SEQ ID NO: 5), K122-4PAK (SEQ ID NO: 6), and CD4 (SEQ ID NO: 7).

EXAMPLES

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Example 1

Bacterial Strains, DNA, and Antibody Sources

The *P. aeruginosa* strains used in this study were PAK, PAK 2Pfs (Bradley, 1974), PAK-BΩ, a 2 kB Ω fragment containing a transcriptional terminator from pHP45 was inserted into the pilB gene, PAK-Ω, the same transcriptional terminator was inserted into the pilD gene (Koga et al., 1993), PAKMS591, the gentamycin cassette from a pPC110 was inserted into the fliC gene (Starnbach et al., 1992), PAKNP the tetracycline cassette from pB322 was inserted into the pilA gene (Saiman et al., 1990), K122-4, a clinical isolate from a cystic fibrosis patient in Toronto which possesses both pili and flagella (Pasloske et al., 1988) and KB7, an isolate containing both pili and flagella (Wong et al., 1995). Several of these strains were generously provided by Dr. Jessica Boyd (NRC Institute for Marine Biosciences, Halifax, Nova Scotia). The strain PAK 2Pfs, a multi-piliated retraction deficient strain, was used for the purification of pili only and not used in experimental conditions. The phenotypes of the *P. aeruginosa* strains with respect to expression of pili was experimentally verified by western blotting with anti-PAK pilus specific anti-sera and by direct ELISA with whole cells and heat inactivated whole cells (to determine the presence of surface exposed pili), by the sensitivity to type IV pilus specific phage, and by monitoring the twitching motility of the strains. *P. aeruginosa* was routinely grown at 37° C. in Luria-Bertani broth (LB) or LB supplemented with 50 μg/ml tetracycline (Sigma-Aldrich, St. Louis, Mo.) for PAKNP, 100 μg/ml of gentamycin for PAKMS591, or 50 μg/ml of streptomycin for strains PAK-BΩ and PAK-DΩ. The polyclonal antibodies generated against the PAK pili and associated pre-immune antisera used in this study have been reported previously (Paranchych et al., 1979).

Example 2

Biotinylation of *P. aeruginosa* Cells and Purified Pili

Biotinylation of bacteria was preformed as previously described by Yu et al. (1996) with the following modifications. Harvested cells were suspended in 5 ml of phosphate buffered saline (PBS) (pH 6.8) with 75 μl of 20 mg/ml biotinamidocaproate N-α-hydroxysuccinimidyl ester dissolved in dimethylsulfoxide and incubated at 22° C. with agitation (200 RPM) in a water bath shaker for 1 hr. Cells were harvested by centrifugation (10,000×g for 10 min at 4° C.) and washed 4 times before resuspension in 1.0 ml PBS, pH 6.8. Viable counts were performed before and after biotinylation. PAK pili were purified from PAK 2Pfs as described previously (Paranchych et al., 1979). The purity and integrity of the pili were assessed by 15% SDS-PAGE (Sambrook et al., 1989) and electron microscopy (FIGS. 1-c, and f). The procedure used for the biotinylation of the purified pili has been previously described (Yu et al., 1996). The ability of the biotinylated pili to bind to asialo-$GM_1$ and $GM_1$ was determined as previously described (Lee et al., 1994) and the binding specificity for asialo-$GM_1$ was confirmed to establish the functional binding activity of the pili following biotinylation.

Example 3

Stainless Steel Binding Assay

Grade 304 stainless steel 2B finish plates (20 gauge-1 mm thick and 7.6 by 11.5 cm) were washed in 95% ethanol for 10 min, and rinsed with distilled water. Immediately before the binding studies, coupons were washed with 20 ml of acetone for one min with gentle agitation and rinsed with distilled water. Coupons were then assembled into a Schleicher and Schuell Minifold™ System (Mandel Scientific Inc. Guelph, Ontario, Canada). Biotinylated viable PAK cells or purified PAK pili (biotinylated or unbiotinylated) were added (100 μl/well in replicates of 6) to the stainless steel manifold and incubated at 37° C. for one hr with gentle agitation. The manifold was subsequently washed 5 times with 250 μl/well Buffer A (PBS pH 7.4 containing 0.05% BSA). Binding was assessed using either streptavidin-horseradish peroxidase (HRP) or polyclonal PAK antibodies and secondary goat-anti-rabbit HRP (BioRad Laboratories Inc. Hercules, Calif.). Substrate buffer (0.01 M sodium citrate buffer pH 4.2 containing 1 mM 2,2'-Azino-bis-[3-ethylbenzthiazoline-6-sulfonic acid] diammonium salt (ABTS) (Sigma-Aldrich, St. Louis, Mo.) and 0.03% (v/v) hydrogen peroxide) was added (125 μl/well) and the manifolds were incubated at RT for 10 min with shaking at 150 rpm. The absorbance was determined at 405 nm using a Multiskan Plus version 2.01 plate reader following transfer of the reaction solution to 96 well flat-bottomed micro titer plates (Corning Inc., Corning, N.Y.).

Example 4

Buccal Epithelial Cell Assay

Buccal epithelial cell assay was completed as described by McEachran and Irvin (1985), with the following modifications. Corning 24-well tissue culture treated ELISA plates were incubated with 500 μl of a 1 μg/ml poly-L-lysine solution at 75° C. overnight before washing for 15 minutes with PBS 3 times. Gluteraldehyde (25%, 125 μl/well) was incubated for one hour at 37° C. Wells were washed as previously stated. Buccal epithelial cells, harvested from 10 healthy volunteers, were filtered through a fine (70 μl) nylon mesh (Nalgene, United States Plastics Corp., Lima, Ohio) and added to the prepared ELISA plate for overnight fixation at 37° C. Binding studies were preformed as noted above.

Example 5

Antibody Inhibition Studies

Biotinylated viable PAK whole cells or biotinylated purified PAK pili were mixed with 50 μl of a $10^{-2}$ dilution of pilus specific antibody (note that all antibodies were initially set to the same titer via an ELISA employing purified pili as an antigen) or pre-immune rabbit sera in PBS buffer, pH 7.4, with a vortex mixer and incubated for one hour at 37° C. The cell or pili mixture was utilized for binding assays as previously described (Yu et al., 1996). Concentrations of biotinylated PAK cells or biotinylated PAK pili ranged from zero to $3.0 \times 10^{16}$ CFU/ml and zero to 1.5 μg/ml respectively. The steel surface was washed five times with Buffer A, incubated with 100 μl of either a rabbit anti-IgG HRP, for the polyclonal antibody or mouse anti-IgG HRP for the monoclonal antibodies. After an one hour incubation at 37° C., the steel surface was washed as described, and ABTS substrate solution (125 μl/well) was added for 15 minutes. The two pilus specific antibodies used in this study, a polyclonal anti-PAK pili antibody (Lee et al., 1989), and monoclonal antibody PK99H (Doig et al., 1990) have been previously described. Rabbit pre-immune serum, which had previously been determined to be free of anti-*Pseudomonas aeruginosa* antibodies by ELISA, was utilized as a control.

Example 6

Peptide Synthesis and Competitive Peptide Inhibition Assays

The peptides described in Table 1 were synthesized as the N-α-acetylated free carboxyl form, except for PAK(134-140) which was synthesized as the N-α-acetylated and C-terminal amide form, by solid-phase peptide synthesis and purified by reversed-phase HPLC as previously reported (Wong et al., 1992; Wong et al., 1995). Peptides containing two cysteine residues were air oxidized to generate the di-sulfide bridged form of the peptide with di-sulfide formation being experimentally confirmed (Campbell et al., 1995). Synthetic peptides PAK(128-144)ox, PAK(117-125), PAK(134-140), PAO (128-144)ox, PAK(128-144)oxT130I, PAO(128-144) ox_Scrambled and PAO(128-144)C129A/C142A_Scrambled were dissolved in Buffer A and incubated with either $10^{15}$ CFU/ml biotinylated viable PAKwt cells or 0.75 μg/ml of biotinylated purified PAK pili such that the final peptide concentration ranged from 51 nM to 51 μM. The samples were then utilized directly in a steel surface binding assay as described above.

Example 7

Trypsinized Bovine Serum Albumin Peptides

Bovine serum albumin (BSA) (Biotech grade, Fisher Scientific Inc., Pittsburgh, Pa.) was dissolved in PBS pH 7.4, and heat denatured by boiling in a water bath for 1 hr. Trypsin (50 μl of a 1 mg/ml solution) was then added to a 10 mg/ml heat denatured BSA solution and incubated at RT overnight with gentle agitation. Trypsin was heat inactivated via boiling water bath for 1 hr before use in competitive peptide inhibition assays as listed above.

Example 8

Direct Binding of Peptides to Steel

To confirm that the pilin receptor binding domain was directly interacting with the steel surface rather than indirectly inhibiting cell or pilus binding to steel, direct binding of the synthetic receptor binding domain was assessed. The binding of the synthetic peptides to steel was determined by a modified immuno-assay that has been previously described (Yu et al., 1996). Synthetic peptides PAK(128-144)ox and PAK(134-140) were prepared in Buffer A (0-51 µM). The peptides were then added directly to wells (100 µl/well in replicates of 6) formed on the steel surface and incubated for one hour at 37° C. without agitation. Following five washes with Buffer A (250 µl/well), a 1:5000 dilution of PK99H was added to each well (100 µl/well) and incubated for one hour, and washed as described. Secondary antibody Goat anti Rabbit IgG HRP (100 µl/well of a 1:3000 dilution) was added and again incubated for one hour. ABTS substrate solution was added (125 µl/well) and allowed to incubate for 25 minutes before the absorbance at 405 nm was determined as described.

Example 9

Acridine Orange Staining and Microscopy

Stainless steel plates, prepared and utilized in bacterial binding studies as described above, were incubated in 1 mM Acridine Orange stain for one minute, and thoroughly rinsed with distilled water. Coupons were visualized using a Leitz laborlux K microscope equipped with a MSP4 camera, and 40× Neoflour lens with epifluorescent illumination. Micrographs were recorded with Kodak Colormax 35 mm film, processed and digitally scanned immediately after film processing.

When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomers and enantiomer of the compound described individual or in any combination.

Many of the molecules disclosed herein contain one or more ionizable groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, reagents, solid substrates, synthetic methods, purification methods, and analytical methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis and additional uses of the invention.

REFERENCES

Arnold, J. W., Boothe, D. H., Suzuki, O., and Bailey, G. W. (2004) Multiple imaging techniques demonstrate the manipulation of surfaces to reduce bacterial contamination and corrosion. *J Microsc* 216: 215-221.

Audette, G. F., Irvin, R. T., and Hazes, B. (2004) Crystallographic analysis of the *Pseudomonas aeruginosa* strain K122-4 monomeric pilin reveals a conserved receptor-binding architecture. *Biochem.* 43: 11427-11435.

Bagge, D., Hjelm, M., Johansen, C., Huber, I., and Gram, L. (2001) *Shewanella putrefaciens* adhesion and biofilm formation on food processing surfaces. *Appl Environ Microbiol* 67: 2319-2325.

Balazs, D. J., Triandafillu, K., Wood, P., Chevolot, Y., van Delden, C., Harms, H., et al. (2004) Inhibition of bacterial adhesion on PVC endotracheal tubes by RF-oxygen glow discharge, sodium hydroxide and silver nitrate treatments. *Biomaterials* 25: 2139-2151.

Beachy, E. H. (1981) Bacterial adherence: adhesion-receptor interactions mediating the attachment of bacteria to mucosal surfaces. *J Infect Dis* 143: 325-345.

Blenkinsopp, S. A., Khoury, A. E., and Costerton, J. W. (1992) Electrical enhancement of biocide efficacy against *Pseudomonas aeruginosa* biofilms. *Appl Environ Microbiol* 58: 3770-3773.

Bodey, G. P., Bolivar, R., Fainstein, V., and Jadeja, L. (1983) Infections caused by *Pseudomonas aeruginosa*. *Rev Infect Dis* 5: 279-313.

Bremer, P. J., and Geesey, G. G. (1991) Laboratory-based model of microbiologically induced corrosion of copper. *Appl Eviron Microbiol* 57: 1956-1962.

Campbell, A. P., McInnes, C., Hodges, R. S., and Sykes, B. D. (1995) Comparison of NMR solution structures of the receptor binding domains of *Pseudomonas aeruginosa* pili strains PAO, KB7, and PAK: implications for receptor binding and synthetic vaccine design. *Biochemistry* 34: 16255-16268.

Characklis, W. G., McFeters, G. A., Marshall, K. C. (1990) Physiological ecology in biofilm systems. In Biofilms. Characklis, W. G., and Marshall, K. C., (eds). New York: John Wiley & Sons, pp. 341-394.

Costerton, J. W. (2001) Cystic fibrosis pathogenesis and the role of biofilms in persistent infection. *Trend Microbiol* 9: 50-52.

Craig, L., Taylor, R. K., Pique, M. E., Adair, B. D., Arvai, A. S., Singh, M., et al. (2003) Type IV pilin structure and assembly: X-ray and EM analysis of Vibrio cholerae toxin-coregulated pilus and *Pseudomonas aeruginosa* PAK pilin. *Mol Cell* 11: 1139-1150.

Doig, P., Sastry, P. A., Hodges, R. S., Lee, K. K., Paranchych, W., and Irvin, R. T. (1990) Inhibition of pilus-mediated adhesion of *Pseudomonas aeruginosa* to human buccal epithelial cells by monoclonal antibodies directed against pili. *Infect Immun* 58: 124-130.

Folkhard, W., Marvin, D. A., Watts T. H., and Paranchych, W. (1981) Structure of polar pili from *Pseudomonas aeruginosa* strains K and O. *J Mol Biol* 149: 79-93.

Groessner-Schreiber, B., Hannig, M., Duck, A., Griepentrog, M., and Wenderoth, D. F. (2004) Do different implant surfaces exposed in the oral cavity of humans show different biofilm compositions and activities? *Eur J Oral Sci* 112: 516-522.

Hazes, B., Sastry, P. A., Hayakawa, K., Read, R. J., and Irvin, R. T. (2000) Crystal structure of *Pseudomonas aeruginosa* PAK pilin suggests a main-chain-dominated mode of receptor binding. *J Mol Biol* 299: 1005-1017.

Hood, S. K., and Zottola, E. A. (1997) Adherence to stainless steel by foodborne microorganisms during growth in model food systems. *Internat J Food Microbiol* 37: 145-153.

Irvin, R. T., Doig, P. C., Lee, K. K., Sastry, P. A., Paranchych, W., Todd, T., and Hodges, R. S. (1989) Characterization of the *Pseudomonas aeruginosa* pilus adhesin: confirmation that the pilin structural protein subunit contains a human epithelial cell-binding domain. *Infect Immun* 57: 3720-3726.

Irvin, R. T., Doig, P. C., Sastry, P. A., Heller, B., and Paranchych, W. (1990) Usefulness of equilibrium parameters of adhesion in predicting the outcome of competition for bacterial receptor sites on respiratory epithelial cells by *Pseudomonas aeruginosa* strains of heterologous pilus type. *Microbial Ecol Health Dis* 3: 39-47.

Johansen, C., Falholt, P., and Gram, L. (1997) Enzymatic removal and disinfection of bacterial biofilms. *Appl Environ Microbiol* 63: 3724-3728.

Khaled, G. H., Finkelstein, F. O., Carey, H. B., Warlaw, S. C., Kilger, A. S., and Edburg, S. C. (2001) Method for studying development of colonization and infection of dialysis catheters. *Adv Perit Dial* 17: 163-171.

Klausen, M., Aaes-Jorgensen, A., Molin, S., and Tolker-Nielsen, T. (2003) Involvement of bacterial migration in the development of complex multicellular structures in *Pseudomonas aeruginosa* biofilms. *Mol Mirobiol* 50: 61-68.

Koga, T., Ishimoto, K., and Lory, S. (1993) Genetic and functional characterization of the gene cluster specifying expression of *Pseudomonas aeruginosa* pili. *Infect Immun* 61: 1371-1377.

Kumon, H., Watanabe, T., Vincent, P., and Nickel, J. C. (1997) Fully hydrated images of *Pseudomonas aeruginosa* biofilm on the surface of catheter material. *Can J Urol* 4: 416-421.

Leake, E. S., Gristina, A. G., and Wright, M. J. (1982) Use of chemotaxis chambers for studying in vitro bacterial colonization of biomaterials. *J Clin Microbiol* 15: 320-323.

Lee, K. K., Sheth, H. B., Wong, W. Y., Sherburne, R., Paranchych, W., Hodges, R. et al. (1994) The binding of *Pseudomonas aeruginosa* pili to glycosphingolipids is a tip-associated event involving the C-terminal region of the structural pilin subunit. *Mol Microbiol* 11: 705-713.

Lee, K. K., Sastry, P. A., Paranchych, W., and Hodges, R. S. (1989) Immunological studies of the disulfide bridge region of *Pseudomonas aeruginosa* PAK and PAO pilins, using anti-PAK pilus and antipeptide antibodies. *Infect Immun* 57: 520-526.

Lomander, A., Schreuders, P., Russek-Cohen, E., and Ali, L. (2004) Evaluation of chlorines' impact on biofilms on scratched stainless steel surfaces. *Bioresour Technol* 94: 275-283.

Mattick, J. S. (2002) Type IV pili and twitching motility. *Ann Rev Microbiol* 56: 289-314.

McEachran, D. W., and Irvin, R. T. (1985) A new method for the irreversible attachment of cells or proteins to polystyrene tissue culture plates for use in the study of bacterial adhesion. *J Microbiol Method* 5: 99-111.

McNeil, S. A., Nordstrom-Lerner, L., Malani, P. N., Zervos, M., and Kauffman, C. A. (2001) Outbreak of sternal surgical site infections due to *Pseudomonas aeruginosa* traced to a scrub nurse with onychomycosis. *Clin Infect Dis* 33: 317-323.

O'Toole, G. A., and Kolter, R. (1998) Flagellar and twitching motility are necessary for *Pseudomonas aeruginosa* biofilm development. *Mol Microbiol* 30: 295-304.

O'Toole, G. A., Kaplan, H. B., and Kolter, R. (2000) Biofilm formation as microbial development. *Annu Rev Microbiol* 54: 49-79.

Paranchych, W., Sastry, P. A., Frost, L. S., Carpenter, M., Armstrong, G. D., and Watts, T. H. (1979) Biochemical studies on pili isolated from *Pseudomonas aeruginosa* strain PAO. *Can J Microbiol* 25: 1175-1181.

Pasloske, B. L., Sastry, P. A., Finlay, B. B., and Paranchych, W. (1988) Two unusual pilin sequences from different isolates of *Pseudomonas aeruginosa*. *J Bacteriol* 170: 3738-3741.

Pier, G. B. (1985) Pulmonary disease associated with *Pseudomonas aeruginosa* in cystic fibrosis: current status of the host-bacterium interaction. *J Infect Dis* 151: 575-580.

Saiman, L., Ishimoto, K., Lory, S., and Prince, A. (1990) The effect of piliation and exoproduct expression on the adherence of *Pseudomonas aeruginosa* to respiratory epithelial monolayers. *J Infect Dis* 161: 541-548.

Sambrook, J., Fritsch, E. F., and Maniatis T. (1989) Molecular cloning: a laboratory manual, 2nd ed. Cold Spring Harbor Laboratory, Cold Spring Harbor, N.Y.

Schweizer, F., Jiao, H., Hindsgual, O., Wong, W., and Irvin, R. T. (1998) Interaction between the pili of *Pseudomonas aeruginosa* PAK and its carbohydrate receptor β-D-Gal-NAc (1-4) β-D-Gal analogs. *Can J Microbiol* 44: 307-311.

Sheth, H. B., Lee, K. K., Wong, W. Y., Srivastava, G., Hindsgaul, O., Hodges, R. S., et al. (1994) The pili of *Pseudomonas aeruginosa* strains PAK and PAO bind specifically to the carbohydrate sequence β GalNAc (1,4) βGal found in glycosphingolipids asialo-GM$_1$ and asialo-GM$_2$. *Mol Microbiol* 11: 715-723.

Sheth, H. B., Glasier, L. M. G., Ellert, N. W., Cachia, P., Kohn, W., Lee, K. K., et al. (1995) Development of an anti-adhesive vaccine for *Pseudomonas aeruginosa* targeting the C-terminal region of the pilin structural protein. Biomed Pept Protein Nucleic Acid 1: 141-148.

Singh, P. K., Schaefer, A. L., Parsek, M. R., Moninger, T. O., Welsh, M. J., and Greenberg, E. P. (2000) Quorum-sensing signals indicate that cystic fibrosis lungs are infected with bacterial biofilms. *Nature* 407: 762-764.

Sreekumari, K. R., Nandakumar, K., and Kikuchi, Y. (2001) Bacterial attachment to stainless steel welds: significance of substratum microstructure. *Biofouling* 17: 303-316.

Stanley, P. M. (1983) Factors affecting the irreversible attachment of *Pseudomonas aeruginosa* to stainless steel. *Can J Microbiol* 29: 1493-1499.

Starnbach, M. N., and Lory, S. (1992) The fliA (rpoF) gene of *Pseudomonas aeruginosa* encodes an alternative sigma factor required for flagellin synthesis. *Mol Microbiol* 6: 459-469.

Stoodley, P., Sauer, K., Davies, D. G., and Costerton, J. W. (2002) Biofilms as complex differentiated communities. *Ann Rev Microbiol* 56: 187-209.

Suci, P. A., and Geesey, G. G. (2001) Comparison of adsorption behavior of two Mytilus edulis foot proteins on three surfaces. *Colloid Surface Biointerface* 22: 159-168.

Traverso, C. E., De Feo, F., Messas-Kaplan, A., Denis, P., Levartovsky, S., Sellem, E., et al. (2005) Long term effect on IOP of a stainless steel glaucoma drainage implant (Ex-PRESS) in combined surgery with phacoemulsification. *Br J Ophthalmol* 89: 425-429.

Tredget, E. E., Shankowsky, H. A., Joffe, A. M., Inkson, T. 1., Volpel, K., Paranchych, W., et al. (1992) Epidemiology of infections with *Pseudomonas aeruginosa* in burn patients: the role of hydrotherapy. *Clin Infect Dis* 15: 941-949.

VanHaecke, E., Remon, J. P., Moors, M., Raes, F., De Rudder, D., and Van Peteghem, A. (1990) Kinetics of *Pseudomonas aeruginosa* adhesion to 304 and 316-L stainless steel: role of cell surface hydrophobicity. *Appl Environ Microb* 56: 788-795.

van Schaik, E. J., Giltner, C. L., Audette, G. F., Keizer, D. W., Bautista, D. L., Slupsky, C. M., et al. (2005) DNA binding: a novel function of *Pseudomonas aeruginosa* type IV pili. *J Bacteriol* 187: 1455-1464.

Watnick, P., and Kolter, R. (2000) Biofilm, city of microbes. *J Bacteriol* 182: 2675-2679.

Wong, W. Y., Campbell, A. P., McInnes, C., Sykes, B. D., Paranchych, W., Irvin, R. T., and Hodges, R. S. (1995) Structure-function analysis of the adherence-binding domain on the pilin of *Pseudomonas aeruginosa* strains PAK and KB7. *Biochemistry* 34: 12963-12972.

Wong, W. Y., Irvin, R. T., Paranchych, W., and Hodges, R. S. (1992) Antigen-antibody interactions: elucidation of the epitope and strain-specificity of a monoclonal antibody directed against the pilin protein adherence binding domain of *Pseudomonas aeruginosa* strain K. *Protein Sci* 1: 1308-1318.

Wozniak, D. J., Wyckoff, T. J., Starkey, M., Keyser, R., Azadi, P., O'Toole, G. A., and Parsek, M. R. (2003) Alginate is not a significant component of the extracellular polysaccharide matrix of PA14 and PAO1 *Pseudomonas aeruginosa* biofilms. *Proc Natl Acad Sci USA* 100: 7907-7912.

Yu, L., Lee, K. K., Paranchych, W., Hodges, R. S., and Irvin, R. T. (1996) Use of synthetic peptides to confirm that the *Pseudomonas aeruginosa* PAK pilus adhesin and the *Candida albicans* fimbrial adhesin possess a homologous receptor-binding domain. *Mol Microbiol* 19: 1107-1116.

Zuo, R., Örnek, D., and Wood, T. K (2005) Aluminum- and mild steel-binding peptides from phage display. *Appl Mirobiol Biotechnol* Epub ahead of print published February 10. DOI: 10.1007/s00253-005-1922-5.

We claim:

1. A method of preventing or inhibiting biofilm formation by a *Pseudomonas* bacteria on a surface, comprising the step of applying to the surface in a carrier, a synthetic pilin peptide containing a C-terminal receptor binding peptide of Type IV *P. aeruginosa* having a core sequence selected from the group consisting of SEQ ID NOS: 2, 3, 4, 5, 6, 7, 14, 15, 17, 18, and 19, in an amount sufficient to prevent or inhibit biofilm formation on the surface.

2. The method of claim 1, wherein the peptide applied to the surface has a core amino acid sequence of K/A/S/T-C-T/K/A-S/T-D/T/N-Q/V/A-D/E-E/P/A/N-Q/M/K-F/Y-I/T/R/L-P-K/N-G/T-C-S/D/T/Q/N-K/N/D/T (SEQ ID NO:2).

3. The method of claim 1, wherein the peptide applied to the surface has a core amino acid sequence selected from the group consisting of SEQ ID NOS:3, 4, 5, 6, 7, 13, 14, 15, 17, 18, and 19.

4. The method of claim 3, wherein the peptide applied to the surface has a core amino acid sequence as set forth in SEQ ID NO:3 or 4.

5. The method of claim 4, wherein the peptide applied to the surface has a core amino acid sequence as set forth in SEQ ID NO:3.

6. The method of claim 1, wherein the carrier agent applied to the surface is phosphate buffer, pH 5-8 containing 10 mM sodium chloride and 1-10% methanol.

7. The method of claim 1, wherein the surface to which the pilin peptide is applied is an abiotic surface.

8. The method of claim 7, wherein the surface to which the pilin peptide is applied is formed of a material selected from the group consisting of stainless steel, tin, aluminum, titanium, chromium, plastic, glass, silicate, ceramics, and a mixture thereof.

9. The method of claim 8, wherein the surface to which the pilin peptide is applied is a stainless steel surface.

10. The method of claim 8, wherein the surface to which the pilin peptide is applied is formed of a polyvinylchloride or polystyrene plastic.

11. The method of claim 1, wherein the biofilm is formed by *Pseudomonas aeroginosa.*

12. A device or an article having a surface treated by the method of claim 1 for preventinq or inhibiting biofilm formation by a *Pseudomonas* bacteria on a surface.

13. The device or the article of claim 12, wherein the device or article is selected from the group consisting of catheter, prosthetic device, contact lens, hydrotherapy pool, pipe, and ship.

* * * * *

SEQUENCE LISTING

```
<160> NUMBER OF SEQ ID NOS: 23

<210> SEQ ID NO 1
<211> LENGTH: 17
<212> TYPE: PRT
<213> ORGANISM: Artificial sequence
<220> FEATURE:
<223> OTHER INFORMATION: Synthetic peptide

<400> SEQUENCE: 1

Lys Cys Thr Ser Thr Gln Asp Glu Gln Phe Ile Pro Lys Gly Cys Ser
1               5                   10                  15

Lys

<210> SEQ ID NO 2
<211> LENGTH: 17
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: X at postion 1 is K, A, S or T.
<220> FEATURE:
<221> NAME/KEY: MISC_FEATURE
<222> LOCATION: (3)..(3)
<223> OTHER INFORMATION: X at postion 3 is T, K or A.
<220> FEATURE:
<221> NAME/KEY: MISC_FEATURE
<222> LOCATION: (4)..(4)
<223> OTHER INFORMATION: X at postion 4 is S or T.
<220> FEATURE:
<221> NAME/KEY: MISC_FEATURE
<222> LOCATION: (5)..(5)
<223> OTHER INFORMATION: X at postion 5 is D, T or N.
<220> FEATURE:
<221> NAME/KEY: MISC_FEATURE
<222> LOCATION: (6)..(6)
<223> OTHER INFORMATION: X at postion 6 is Q, V or A.
<220> FEATURE:
<221> NAME/KEY: MISC_FEATURE
<222> LOCATION: (7)..(7)
<223> OTHER INFORMATION: X at postion 7 is D or E.
<220> FEATURE:
<221> NAME/KEY: MISC_FEATURE
<222> LOCATION: (7)..(7)
<223> OTHER INFORMATION: X at postion 7 is D or E.
<220> FEATURE:
<221> NAME/KEY: MISC_FEATURE
<222> LOCATION: (8)..(8)
<223> OTHER INFORMATION: X at postion 8 is E, P, A or N.
<220> FEATURE:
<221> NAME/KEY: MISC_FEATURE
<222> LOCATION: (9)..(9)
<223> OTHER INFORMATION: X at postion 9 is Q, M or K.
<220> FEATURE:
<221> NAME/KEY: MISC_FEATURE
<222> LOCATION: (10)..(10)
<223> OTHER INFORMATION: X at postion 10 is Y or F.
<220> FEATURE:
<221> NAME/KEY: MISC_FEATURE
<222> LOCATION: (11)..(11)
<223> OTHER INFORMATION: X at postion 11 is I, T, R or L.
<220> FEATURE:
<221> NAME/KEY: MISC_FEATURE
<222> LOCATION: (13)..(13)
<223> OTHER INFORMATION: X at postion 13 is K or N.
<220> FEATURE:
<221> NAME/KEY: MISC_FEATURE
<222> LOCATION: (14)..(14)
<223> OTHER INFORMATION: X at postion 14 is G or T.
<220> FEATURE:
<221> NAME/KEY: MISC_FEATURE
<222> LOCATION: (16)..(16)
<223> OTHER INFORMATION: X at postion 16 is S, D, T, Q or N.
<220> FEATURE:
<221> NAME/KEY: MISC_FEATURE
<222> LOCATION: (17)..(17)
<223> OTHER INFORMATION: X at postion 17 is K, N, D or T.

<400> SEQUENCE: 2

Xaa Cys Xaa Xaa Xaa Xaa Xaa Xaa Xaa Xaa Xaa Pro Xaa Xaa Cys Xaa
1               5                   10                  15

Xaa

<210> SEQ ID NO 3
<211> LENGTH: 17
<212> TYPE: PRT
<213> ORGANISM: Artificial sequence
<220> FEATURE:
<223> OTHER INFORMATION: Synthetic peptide

<400> SEQUENCE: 3

Lys Cys Thr Ser Asp Gln Asp Glu Gln Phe Ile Pro Lys Gly Cys Ser
1               5                   10                  15
```

Lys

```
<210> SEQ ID NO 4
<211> LENGTH: 17
<212> TYPE: PRT
<213> ORGANISM: Artificial sequence
<220> FEATURE:
<223> OTHER INFORMATION: Synthetic peptide

<400> SEQUENCE: 4

Ala Cys Lys Ser Thr Gln Asp Pro Met Phe Thr Pro Lys Gly Cys Asp
1               5                   10                  15
Asn

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Ser Cys Ala Thr Thr Val Asp Ala Lys Phe Arg Pro Asn Gly Cys Thr
1               5                   10                  15
Asp

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Ala Cys Thr Ser Asn Ala Asp Asn Lys Tyr Leu Pro Lys Thr Cys Gln
1               5                   10                  15
Thr

<210> SEQ ID NO 7
<211> LENGTH: 17
<212> TYPE: PRT
<213> ORGANISM: Artificial sequence
<220> FEATURE:
<223> OTHER INFORMATION: Synthetic peptide

<400> SEQUENCE: 7

Thr Cys Thr Ser Thr Gln Glu Glu Met Phe Ile Pro Lys Gly Cys Asn
1               5                   10                  15
Lys

<210> SEQ ID NO 8
<211> LENGTH: 7
<212> TYPE: PRT
<213> ORGANISM: Artificial sequence
<220> FEATURE:
<223> OTHER INFORMATION: Synthetic peptide

<400> SEQUENCE: 8

Asp Glu Gln Phe Ile Pro Lys
1               5

<210> SEQ ID NO 9
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 9

Thr Leu Thr Arg Thr Ala Ala Asp Gly
1               5

<210> SEQ ID NO 10
<211> LENGTH: 31
<212> TYPE: PRT
<213> ORGANISM: Artificial sequence
<220> FEATURE:
<223> OTHER INFORMATION: Synthetic peptide

<400> SEQUENCE: 10

Pro Gln Tyr Gln Asn Tyr Val Ala Arg Ser Glu Gly Ala Ser Ala Leu
1               5                   10                  15

Ala Ser Val Asn Pro Leu Lys Thr Thr Val Glu Glu Ala Asp Pro
            20                  25                  30

<210> SEQ ID NO 11
<211> LENGTH: 17
<212> TYPE: PRT
<213> ORGANISM: Artificial sequence
<220> FEATURE:
<223> OTHER INFORMATION: Synthetic peptide

<400> SEQUENCE: 11

Asn Cys Pro Asp Phe Asp Pro Thr Lys Lys Gly Met Gln Ala Cys Thr
1               5                   10                  15

Ser

<210> SEQ ID NO 12
<211> LENGTH: 17
<212> TYPE: PRT
<213> ORGANISM: Artificial sequence
<220> FEATURE:
<223> OTHER INFORMATION: Synthetic peptide

<400> SEQUENCE: 12

Asn Ala Pro Asp Phe Asp Pro Thr Lys Lys Gly Met Gln Ala Ala Thr
1               5                   10                  15

Ser

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Ala Cys Ile Ser Thr Gln Asp Pro Met Phe Thr Pro Lys Gly Cys Asp
1               5                   10                  15

Asn

<210> SEQ ID NO 14
<211> LENGTH: 23
<212> TYPE: PRT
<213> ORGANISM: Artificial sequence
<220> FEATURE:
<223> OTHER INFORMATION: Synthetic peptide

<400> SEQUENCE: 14

Asn Cys Lys Ile Thr Lys Thr Pro Thr Ala Trp Lys Pro Asn Tyr Ala
```

Pro Ala Asn Cys Pro Lys Ser
            20

<210> SEQ ID NO 15
<211> LENGTH: 23
<212> TYPE: PRT
<213> ORGANISM: Artificial sequence
<220> FEATURE:
<223> OTHER INFORMATION: Synthetic peptide

<400> SEQUENCE: 15

Thr Cys Ala Thr Ser Gly Ser Pro Ala Asn Trp Lys Ala Asn Tyr Ala
1               5                   10                  15

Pro Ala Asn Cys Pro Lys Ser
            20

<210> SEQ ID NO 16
<211> LENGTH: 17
<212> TYPE: PRT
<213> ORGANISM: Artificial sequence
<220> FEATURE:
<223> OTHER INFORMATION: Synthetic peptide

<400> SEQUENCE: 16

Ser Cys Ala Thr Thr Val Asp Ala Lys Phe Arg Pro Asn Gly Cys Thr
1               5                   10                  15

Asp

<210> SEQ ID NO 17
<211> LENGTH: 35
<212> TYPE: PRT
<213> ORGANISM: Artificial sequence
<220> FEATURE:
<223> OTHER INFORMATION: Synthetic peptide

<400> SEQUENCE: 17

Gly Cys Ala Ser Asp Ser Asn Ala Val Ser Ser Gly Thr Asp Arg Asn
1               5                   10                  15

Met Pro Ala Leu Thr Ala Gly Thr Leu Pro Ala Arg Phe Ala Pro Ser
            20                  25                  30

Glu Cys Arg
        35

<210> SEQ ID NO 18
<211> LENGTH: 28
<212> TYPE: PRT
<213> ORGANISM: Artificial sequence
<220> FEATURE:
<223> OTHER INFORMATION: Synthetic peptide

<400> SEQUENCE: 18

Ala Cys Gly Asn Ala Ser Ile Asp Gly Phe Ala Gly Thr Gly Thr Thr
1               5                   10                  15

Ile Asp Ala Lys Tyr Leu Pro Asn Ala Cys Lys Pro
            20                  25

<210> SEQ ID NO 19
<211> LENGTH: 32
<212> TYPE: PRT
<213> ORGANISM: Artificial sequence
<220> FEATURE:
<223> OTHER INFORMATION: Synthetic peptide

<400> SEQUENCE: 19

```
Ala Cys Thr Ser Ala Ser Asn Ala Thr Ala Gln Phe Thr Gly
1               5                   10                  15

Met Ala Ala Gly Ser Val Pro Gln Glu Phe Ala Pro Ala Gln Cys Arg
            20                  25                  30
```

<210> SEQ ID NO 20
<211> LENGTH: 144
<212> TYPE: PRT
<213> ORGANISM: Pseudomonas aeruginosa

<400> SEQUENCE: 20

```
Phe Thr Leu Ile Glu Leu Met Ile Val Val Ala Ile Ile Gly Ile Leu
1               5                   10                  15

Ala Ala Ile Ala Ile Pro Gln Tyr Gln Asn Tyr Val Ala Arg Ser Glu
            20                  25                  30

Gly Ala Ser Ala Leu Ala Ser Val Asn Pro Leu Lys Thr Thr Val Glu
        35                  40                  45

Glu Ala Leu Ser Arg Gly Trp Ser Val Lys Ser Gly Thr Gly Thr Glu
    50                  55                  60

Asp Ala Thr Lys Lys Glu Val Pro Leu Gly Val Ala Asp Ala Asn
65                  70                  75                  80

Lys Leu Gly Thr Ile Ala Leu Lys Pro Asp Pro Ala Asp Gly Thr Ala
                85                  90                  95

Asp Ile Thr Leu Thr Phe Thr Met Gly Gly Ala Gly Pro Lys Asn Lys
            100                 105                 110

Gly Lys Ile Ile Thr Leu Thr Arg Thr Ala Ala Asp Gly Leu Trp Lys
        115                 120                 125

Cys Thr Ser Asp Gln Asp Glu Gln Phe Ile Pro Lys Gly Cys Ser Arg
    130                 135                 140
```

<210> SEQ ID NO 21
<211> LENGTH: 143
<212> TYPE: PRT
<213> ORGANISM: Pseudomonas aeruginosa

<400> SEQUENCE: 21

```
Phe Thr Leu Ile Glu Leu Met Ile Val Val Ala Ile Ile Gly Ile Leu
1               5                   10                  15

Ala Ala Ile Ala Ile Pro Gln Tyr Gln Asn Tyr Val Ala Arg Ser Glu
            20                  25                  30

Gly Ala Ser Ala Leu Ala Thr Ile Asn Pro Leu Lys Thr Thr Val Glu
        35                  40                  45

Glu Ser Leu Ser Arg Gly Ile Ala Gly Ser Lys Ile Lys Ile Gly Thr
    50                  55                  60

Thr Ala Ser Thr Ala Thr Glu Thr Tyr Val Gly Val Glu Pro Asp Ala
65                  70                  75                  80

Asn Lys Leu Gly Val Ile Ala Val Ala Ile Glu Asp Ser Gly Ala Gly
                85                  90                  95

Asp Ile Thr Phe Thr Phe Gln Thr Gly Thr Ser Ser Pro Lys Asn Ala
            100                 105                 110

Thr Lys Val Ile Thr Leu Asn Arg Thr Ala Asp Gly Val Trp Ala Cys
        115                 120                 125

Lys Ser Thr Gln Asp Pro Met Phe Thr Pro Lys Gly Cys Asp Asn
    130                 135                 140
```

<210> SEQ ID NO 22
<211> LENGTH: 148

```
<212> TYPE: PRT
<213> ORGANISM: Pseudomonas aeruginosa

<400> SEQUENCE: 22

Phe Thr Leu Ile Glu Leu Met Ile Val Val Ala Ile Gly Ile Leu
1               5                   10                  15

Ala Ala Ile Ala Ile Pro Ala Tyr Gln Asp Tyr Thr Ser Arg Ser Gln
            20                  25                  30

Val Ser Arg Val Met Ala Glu Ala Gly Ser Leu Lys Thr Ala Val Glu
        35                  40                  45

Ala Cys Leu Gln Asp Gly Arg Thr Ala Val Gly Thr Ala Ala Gly Gln
50                  55                  60

Cys Asp Pro Gly Ala Thr Gly Ser Ser Leu Leu Thr Gly Ala Ser Gln
65                  70                  75                  80

Thr Ser Gln Thr Leu Pro Thr Asn Thr Gly Val Pro Gln Val Leu Asp
                85                  90                  95

Pro Leu Thr Thr Gln Thr Thr Ile Ile Val Thr Phe Gly Asn Gly Ala
            100                 105                 110

Ser Ala Ala Ile Ser Gly Gln Thr Leu Thr Trp Thr Arg Asp Val Asn
        115                 120                 125

Gly Gly Trp Ser Cys Ala Thr Thr Val Asp Ala Lys Phe Arg Pro Asn
130                 135                 140

Gly Cys Thr Asp
145

<210> SEQ ID NO 23
<211> LENGTH: 150
<212> TYPE: PRT
<213> ORGANISM: Pseudomonas aeruginosa

<400> SEQUENCE: 23

Phe Thr Leu Ile Glu Leu Met Ile Val Val Ala Ile Gly Ile Leu
1               5                   10                  15

Ala Ala Ile Ala Ile Pro Ala Tyr Gln Asp Tyr Thr Ala Arg Ala Gln
            20                  25                  30

Leu Ser Glu Ala Met Thr Leu Ala Ser Gly Leu Lys Thr Lys Val Ser
        35                  40                  45

Asp Ile Phe Ser Gln Asp Gly Ser Cys Pro Ala Asn Thr Ala Ala Thr
50                  55                  60

Ala Gly Ile Glu Lys Asp Thr Asp Ile Asn Gly Lys Tyr Val Ala Lys
65                  70                  75                  80

Val Thr Thr Gly Gly Thr Ala Ala Ser Gly Gly Cys Thr Ile Val
                85                  90                  95

Ala Thr Met Lys Ala Ser Asp Val Ala Thr Pro Leu Arg Gly Lys Thr
            100                 105                 110

Leu Thr Leu Thr Leu Gly Asn Ala Asp Lys Gly Ser Tyr Thr Trp Ala
        115                 120                 125

Cys Thr Ser Asn Ala Asp Asn Lys Tyr Leu Pro Lys Thr Cys Gln Thr
130                 135                 140

Ala Thr Thr Thr Pro
145             150
```